US008551474B2

(12) United States Patent
Link, Jr. et al.

(10) Patent No.: US 8,551,474 B2
(45) Date of Patent: Oct. 8, 2013

(54) ANTITUMOR VACCINATION USING ALLOGENEIC TUMOR CELLS EXPRESSING ALPHA (1,3)-GALACTOSYLTRANSFERASE

(75) Inventors: Charles J. Link, Jr., Clive, IA (US); Tatiana Seregina, West Des Moines, IA (US); Gabriela Rossi, Ankeny, IA (US)

(73) Assignee: Central Iowa Health System, Des Moines, IA (US)

( * ) Notice: Subject to any disclaimer, the term of this patent is extended or adjusted under 35 U.S.C. 154(b) by 431 days.

(21) Appl. No.: 12/890,178

(22) Filed: Sep. 24, 2010

(65) Prior Publication Data
US 2011/0086067 A1    Apr. 14, 2011

Related U.S. Application Data

(63) Continuation of application No. 11/013,685, filed on Dec. 16, 2004, now abandoned, which is a continuation-in-part of application No. 10/682,178, filed on Oct. 9, 2003, now abandoned.

(60) Provisional application No. 60/417,343, filed on Oct. 9, 2002.

(51) Int. Cl.
*A01N 63/00* (2006.01)
*A01N 63/02* (2006.01)
*C12N 5/09* (2010.01)
*C12N 5/10* (2006.01)
*C12N 5/02* (2006.01)
*C12N 5/07* (2010.01)
*A61K 35/00* (2006.01)

(52) U.S. Cl.
CPC .. *A61K 35/13* (2013.01); *C12N 5/10* (2013.01)
USPC ..... 424/93.7; 424/93.1; 424/93.2; 424/93.21; 424/93.3; 424/277.1; 435/325; 435/347; 435/366

(58) Field of Classification Search
USPC ................. 424/93.1, 93.2, 93.21, 93.3, 93.7, 424/277.1; 435/325, 347, 366
See application file for complete search history.

(56) References Cited

U.S. PATENT DOCUMENTS

| | | |
|---|---|---|
| 5,869,035 A | 2/1999 | Link, Jr. et al. |
| 5,879,675 A | 3/1999 | Galili |
| 6,187,306 B1 | 2/2001 | Pardoll et al. |
| 6,218,166 B1 | 4/2001 | Ravindranath et al. |
| 6,333,028 B1 | 12/2001 | Berd |
| 6,361,775 B1 | 3/2002 | Galili |
| 6,713,055 B2 | 3/2004 | Schiff |
| 7,005,126 B1 | 2/2006 | Link, Jr. et al. |
| 7,740,837 B2 | 6/2010 | Fahrai |
| 7,763,461 B2 | 7/2010 | Link, Jr. et al. |
| 2004/0191229 A1 | 9/2004 | Link, Jr. et al. |
| 2005/0201993 A1 | 9/2005 | Link, Jr. et al. |
| 2007/0014775 A1 | 1/2007 | Link, Jr. et al. |

FOREIGN PATENT DOCUMENTS

WO    WO 95/24924    9/1995

OTHER PUBLICATIONS

Morris, J.C., et al., Journal of Clinical Oncology, Phase I study of an antitumor vaccination using alpha(1,3) galactosyltransferase expressing allogeneic tumor cells in patients (Pts) with refractory or recurrent non-small cell lung cancer (NSCLC), ASCO Annual Meeting Proceedings, 23(16S): 2586, 2005, Abstract, 1 page.
Chapter 4, Reverse Transcriptase and the Generation of Retroviral DNA. Retroviruses, Ed John Coffin, Stephen Huges and Harold Varmus, 1997, Cold Spring Harbor Laboratory Press, pp. 121-129.
Improved Retroviral Vectors for Gene Transfer and Expression. A. Dusty Miller and Guy H. Rosman Biotechniques, Author manuscript, available in PMC Feb. 3, 2006. PMCID: PMC1360503 Published in final edited form as: Biotechniques. Oct. 7, 1989(9): 980-990.
Genbank entry for M28247.1 at the National Center for Biotechnology Informaion. Submitted Sep. 22, 1989.
Genbank entry for X05157.1 at the National Center for Biotechnology Information. J. Gen. Virol. 68 (PT3), 683-693.
Genbank entry for X05161.1 at the National Center for Biotechnology Information J. Gen. Virol. 68 (PT 3) 683-693 (1987).
Larsen, R.D. et al (1989) "Isolation of a cDNA encoding a murine UDPgalactose:beta-D-galactosyl-1,4-N-acetyl-D-glucosaininide alpha-1,3-galctosyltransferase: expression clonging by gene transfer," Proc. Natl. Acad. Sci., USA, 86:8277-8231.
ATCC Cell Lines and Hybridomas, Eight Edition, 1984, edited by Robert Hey, PhD, et al. published γ American Type Culture Collection, Rockville, Maryland, USA (1984), 4 pages.
ATCC Cell Lines and Hybridomas, 8$^{th}$ Ed, 1994 p. 100.
Chamberlain, R.S. et al. (2000) "Innovations and Strategies for the Development of Anti-Cancer Vaccines," Expert Opinion on Pharmacotherapy, 1(4):603-614.
International Search Report for PCT/US03/32036.
Galili et al. (2001) "Preparation of autologous leukemia and lymphoma vaccines expressing alpha-gal epitopes," J. Hematother. and Stem Cell Res. 10(4):501-511.
LaTemple, et al. (1996) "Synthesis of α-Galactosyl Epitopes by Recombinant α1,3Galactosyltransferase for Opsonization for Human Tumor Cell Vaccines by Anti-Galactose," Cancer Res. 56:3069-3074.
LaTemple, et al. (1999) "Increased Immunogenicity of Tumor Vaccines Complexed with Anti-gal: Studies in Knockout Mice for α1,3galactosyltransferse," Cancer Res. 59(4):3417-3423.
Gorelik, et al. (1995) "Alterations of Cell Surface Carbohydrates and Inhibition of Metastatic Property of Murine Melanomas by α1,3galactosyl gene transfection," Cancer Res., 55(18):4168-4173.
Galili et al. (2003) "Expression of α-gal Epitopes on Ovarian Carcinoma Membranes to be Used as a Novel Autologous Tumor Vaccine," Gynecologic Oncology, 90(1):100-108.

(Continued)

*Primary Examiner* — Misook Yu
*Assistant Examiner* — Anne Holleran
(74) *Attorney, Agent, or Firm* — Cooley LLP

(57) ABSTRACT

The invention relates to methods and compositions for causing the selective targeting and killing of tumor cells. Through ex vivo gene therapy protocols tumor cells are engineered to express an α(1,3)galactosyl epitope. The cells are then irradiated or otherwise killed and administered to a patient. The α-galactosyl epitope causes opsonization of the tumor cell enhancing uptake of the opsonized tumor cell by antigen presenting cells which results in enhanced tumor specific antigen presentation. The animal's immune system thus is stimulated to produce tumor specific cytotoxic cells and antibodies which will attack and kill tumor cells present in the animal.

12 Claims, 31 Drawing Sheets

(56) References Cited

OTHER PUBLICATIONS

Yoshimura et al. (2001) "Expression of Xenoantigen Transformed Human Cancer Cells to be Susceptible to Antibody-Mediated Cell Killing," Cancer Letters, 164(2):155-160.

van Elsas et al (2001) "Elucidating the Autoimmune and Antitumor Effector Mechanisms of a Treatment Based on Cytotoxic T Lymphocyte Antigen-4 Blockade in Combination with a B16 Melanoma Vaccine: Comparison of Prophylaxis and Therapy," J. Exp. Med. 194(4):481-489.

Tratschin et al. (1985) "Adeno-associated virus vector for high-frequency integration, expression, and rescue of genes in mammalian cells," Mol. Cell Biol. 5(11):3251-3260.

Non-Final Office Action issued on Jan. 3, 2007 in connection with U.S. Appl. No. 10/682,178.

Final Office Action issued on Jun. 18, 2007 in connection with U.S. Appl. No. 10/682,178.

Non-Final Office Action issued on Apr. 29, 2008 in connection with U.S. Appl. No. 10/682,178.

Non-Final Office Action issued on Dec. 12, 2008 in connection with U.S. Appl. No. 10/682,178.

Final Office Action issued on Jul. 27, 2009 in connection with U.S. Appl. No. 10/682,178.

Non-Final Office Action issued on Jul. 5, 2007 in connection with U.S. Appl. No. 11/013,685.

Non-Final Office Action issued on Jan. 3, 2008 in connection with U.S. Appl. No. 11/013,685.

Final Office Action issued on Aug. 6, 2008 in connection with U.S. Appl. No. 11/013,685.

Non-Final Office Action issued on Feb. 5, 2009 in connection with U.S. Appl. No. 11/013,685.

Final Office Action issued on Aug. 24, 2009 in connection with U.S. Appl. No. 11/013,685.

Non-Final Office Action issued on Oct. 9, 2007 in connection with U.S. Appl. No. 11/533,184.

Non-Final Office Action issued on Apr. 30, 2008 in connection with U.S. Appl. No. 11/533,184.

Non- Final Office Action issued on Dec. 12, 2008 in connection with U.S. Appl. No. 11/533,184.

Non-Final Office Action issued on Oct. 9, 2007 in connection with U.S. Appl. No. 12/533,199.

Non-Final Office Action issued on Jan. 3, 2008 in connection with U.S. Appl. No. 12/533,199.

Final Office Action issued on Aug. 26, 2008 in connection with U.S. Appl. No. 12/533,199.

Non-Final Office Action issued on Feb. 4, 2009 in connection with U.S. Appl. No. 12/533,199.

Final Office Action issued on Aug. 10, 2009 in connection with U.S. Appl. No. 12/533,199.

```
   1 tttgaaagac cccacccgta ggtggcaagc tagcttaagt aacgccactt tgcaaggcat
  61 ggaaaaatac ataactgaga ataqaaaagt tcagatcaag gtcaggaaca aagaaacagc
 121 tgaataccaa acaggatatc tgtggtaagc ggttcctgcc ccggctcagg gccaagaaca
 181 gatgagacag ctgagtgatg ggccaaacag gatatctgtg gtaagcagtt cctgcccggg
 241 ctcggggcca agaacagatg gtccccagat gcggtccagc cctcagcagt ttctagtgaa
 301 tcctcagatg tttccagggt gcccaagga cctgaaaatg accctgtacc ttatttgaac
 361 taaccaatca gttcgcttct cgcttctgtt cgcgcgctcc cgctctccga gctcaataaa
 421 agagcccaca accctcact cggcgcgcca gtcttccgat agactgcgtc gcccgggtac
 481 ccgtattccc aataaagcct cttgctgttt gcatccgaat cgtggtctcg ctgttccttg
 541 ggagggtctc ctctgagtga ttgactaccc acgacggggg tgcagcattc tccagtgggg
 601 gctcgtccgg gatttggaga ccctgccca gggaccacgg accaccacc gggaggtaag
 661 ctggccagca acttatctgt gtctgtccga ttgtctagtg tctatgtttg atgttatgcg
 721 cctgcgnctg tactagttag ctaantagct ctgtatctgg cggacccgtg gtggaactga
 781 cgagttctga acacccggcc gcaaccctgg gagacgtccc agggactttg gggccgttt
 841 ttgtggccgg acctgaggaa gggagtcgat gtggaatcgn acccgtcag gatatgtggt
 901 tctggtagga gacgagaacc taaaacagtt cccgcctccg tctgaatttt tgctttcggt
 961 ttggaaccga agccgcgcgt cntgtctgct gcagcgctgc agcatcgttc tgtgttgtct
1023 ctgtctgact gtgttctgt attgtctga aaattagggc cagactgtta ccactccctt
1081 aagtttgacc ttaggtcact ggaaagatgt cgagcggatc gctcacaacc agtcggtaga
1141 tgtcaagaag agacgttggg ttacctctg ctctgcagaa tggccaacct ttaacgtcgg
1201 atggccgcga gacggcacct ttaaccgaga cctcatcacc caggttaaga tcaagtctt
1261 ttcacctggc ccgcatggac acccagacca ggtcccctac atcgtgacct gggaagcctt
1321 ggcttttgac ccccctcct gggtcaagcc cnngtacac cctaagccte cgcctcctct
1381 tcctccatcc gccccgtctc tccccttga acctcctcgt tcgaccccgc ctcgatcctc
1441 cctttatcca gcccctcactc cttctctagg cgccggaatt ccgatctgat caagagacag
1501 gatgaggatc gnttcgcatg attgaacaag atggattgca cgcaggttct ccggccgcnt
1561 gggtggagag gctattcgg tatgactggg cacaacagac aatcggctgc tctgatgccg
1621 ccgtgttccg gctgtcagcg caggggcgcc cggttcttt tgtcaagacc gacctgtccg
1681 gtgccctgaa tgaactgcag gacgaggcag cgcggctatc gtggctggcc acgacgggcg
1741 ttccttgcgc agctgtgctc gacgttgtca ctgaagcggg aagggactgg ctgctattgg
1801 gcgaagtgcc ggggcaggat ctcctgtcat ctcaccttgc tcctgccgag aaagtatcca
1861 tcatggctga tgcaatgcgg cggctgcata cgcttgatcc ggctacctgc ccattcgacc
1921 accaagcgaa acatcgcatc gagcgagcac gtactcggat ggaagccggt cttgtcgatc
1981 aggatgatct ggacgaagag catcagggc tcgcgccagc cgaactgttc gccaggctca
2041 aggcgcgcat gcccgacggc gaggatctcg tcgtgaccca tggcgatgcc tgcttgccga
2101 atatcatggt ggaaaatggc cgcttttctg gattcatcga ctgtggccgg ctgggtgtgg
2161 cggaccgcta tcaggacata gcgttggcta cccgtgatat tgctgaagag cttggcggcg
2221 aatgggctga ccgcttcctc gtgctttacg gtatcgccgc tcccgattcg cagcgcatcg
2281 ccttctatcg ccttcttgac gagttcttct gagcgggact ctgggttcg aaatgaccga
2341 ccaagcgacg cccaacctgc catcacgaga tttcgattcc accgccgcct ctatgaaag
2401 gttgggcttc ggaatcgttt tccgggacgc cggctggatg atcctccagc gcggggatct
2461 catgctggag ttcttcgccc accccggct cgatccctc gcgagttggt tcagctgctg
2521 cctgaggctg gacgacctcg cggagttcta cggcagtgc aaatccgtcg gcatccagga
2581 aaccagcagc ggctatccga gcatcatgc acccgaactg caggagtggg gaggcacgat
2641 ggccgcttg gtcgaggcgg atccggccat tagccatatt attcattggt tatatagcat
2701 aaatcaatat tggctattgg ccattgcata cgttgtatcc atatcataat atgtacanti
2761 atatggctc atgtccaaca ttaccgccat gttgacattg attattgact agttattaat
2821 agtaatcaat tacggggtca ttagttcata gcccatatat ggagttccg gttacataac
2881 ttacggtaaa tggcccgcct ggctgaccgc ccaacgaccc ccgcccattg acgtcaataa
2941 tgacgtatgt tcccatagta acgccaatag ggactttcca ttgacgtcaa tgggtggagt
3001 atttacggta aactgcccac ttggcagtac atcaagtgta tcatatgcca agtacgcccc
3061 ctattgacgt caatgacggt aaatggcccg cctggcatta tgcccagtac atgaccttat
3121 gggactttcc tacttggcag tacatctacg tattagtcat cgctattacc atggtgatgc
3181 ggttttggca gtacatcaat gggcgtggat agcggtttga ctcacgggga tttccaagtc
```

*Fig.2A*

```
3241 tccaccccat tgacgtcaat gggagtttgt tttggcacca aaatcaacgg gactttccaa
3301 aatgtcgtaa caactccgcc ccattgacgc aaatgggcgg taggcatgta cggtgggagg
3361 tctatataag cagagctcgt ttagtgaacc gtcagatcgc ctggagacgc catccacgct
3421 gttttgacct ccatagaaga caccgggacc gatccagcct ccgcggcccc aagcttgaca
3481 tggatgtcaa gggaaaagta atcctgttga tgctgattgt ctcaaccgtg gttgtcgtgt
3541 tttgggaata tgtcaacaga attccagagg ttggtgagaa cagatggcag aaggactggt
3601 ggttcccaag ctggtttaaa aatgggaccc acagttatca agaagacaac gtagaaggac
3661 ggagagaaaa gggtagaaat ggagatcgca ttgaagagcc tcagctatgg gactggttca
3721 atccaaagaa ccgcccggat gttttgacag tgaccccgtg gaaggcgccg attgtgtggg
3781 aaggcactta tgacacagct ctgctggaaa agtactacgc cacacagaaa ctcactgtgg
3841 ggctgacagt gtttgctgtg ggaaagtaca ttgagcatta cttagaagca tttctggagt
3901 ctgctgacat gtacttcatg gttggccatc gggtcatatt ttacgtcatg atagatgaca
3961 cctcccggat gcctgtcgtg cacctgaacc ctctacattc cttacaagtc tttgagatca
4021 ggtctgagaa gaggtggcag gatatcagca tgatgcgcat gaagaccatt gggagcaca
4081 tcctggccca catccagcac gaggtcgact tcctcttctg catggacgtg gatcaagtct
4141 ttcaagacaa cttcgggggtg gaaactctgg gccagctggt agcacagctc caggcctggt
4201 ggtacaaggc cagtcccgag aagttcaccct atgagaggcg ggaactgtcg gccgcgtaca
4261 ttccattcgg agaggggggat ttttactacc acgcggccat ttttggagga acgcctactc
4321 acattctcaa cctcaccagg gagtgcttta aggggatcct ccaggacaag aaacatgaca
4381 tagaagccca gtggcatgat gagagccacc tcaacaaata cttccttttc aacaaaccca
4441 ctaaaatcct atctccagag tattgctggg actatcagat aggcctgcct tcagatatta
4501 aaagtgtcaa ggtagcttgg cagacaaaag agtataattt ggttagaaat aatgtctgaa
4561 tcgataaaat aaaagatttt atttagtctc cagaaaaagg ggggaatgaa agaccccacc
4621 tgtaggtttg gcaagctagc ttaagtaacg ccattttgca aggcatggaa aaatacataa
4681 ctgagaatag agaagttcag atcaaggtca ggaacagatg gaacagctga atatgggcca
4741 aacaggatat ctgtggtaag cagttcctgc cccggctcag ggccaagaac agatggaaca
4801 gctgaatatg ggccaaacag gatatctgtg gtaagcagtt cctgccccgg ctcagggcca
4861 agaacagatg gtccccagat gcggtccagc cctcagcagt ttctagagaa ccatcagatg
4921 tttccagggt gccccaagga cctgaaatga ccctgtgcct tatttgaact aaccaatcag
4981 ttcgcttctc gcttctgttc gcgcgcttct gctccccgag ctcaataaaa gagcccacaa
5041 cccctcactc ggggcgccag tcctccgatt gactgagtcg cccgggtacc cgtgtatcca
5101 ataaaccctc ttgcagttgc atccgacttg tggtctcgct gttccttggg agggtctcct
5161 ctgagtgatt gactaccgt cagcgggggt ctttcatttg gggctcgtc cgggatcggg
5221 agaccctgc ccagggacca ccgacccacc accggaggt aagctggctg cctcgcgcgt
5281 ttcggtgatg acggtgaaaa cctctgacac atgcagctcc cggagacggt cacagcttgt
5341 ctgtaagcgg atgccggag cagacaagcc cgtcagggcg cgtcagcggg tgttggcggg
5401 tgtcggggcg cagccatgac ccagtcacgt agcgatagcg gagtgtatac tggcttaact
5461 atgcggcatc agagcagatt gtactgagag tgcaccatat gcggtgtgaa ataccgcaca
5521 gatgcgtaag gagaaaatac cgcatcaggc gctcttccgc ttcctcgctc actgactcgc
5581 tgcgctcggt cgttcggctg cggcgagcgg tatcagctca ctcaaaggcg gtaatacggt
5641 tatccacaga atcagggat aacgcaggaa agaacatgtg agcaaaaggc cagcaaaagg
5701 ccaggaaccg taaaaaggcc gcgttgctgg cgtttttcca taggctccgc cccctgacg
5761 agcatcacaa aatcgacgc tcaagtcaga ggtggcgaaa cccgacagga ctataaagat
5821 accaggcgtt tccccctgga agctccctcg tgcgctctcc tgttccgacc ctgccgctta
5881 ccggatacct gtccgccttt ctcccttcgg gaagcgtggc gctttctcat agctcacgct
5941 gtaggtatct cagttcggtg taggtcgttc gctccaagct gggctgtgtg cacgaaccc
6001 ccgttcagcc cgaccgctgc gccttatccg gtaactatcg tcttgagtcc aacccggtaa
6061 gacacgactt atcgccactg gcagcagcca ctggtaacag gattagcaga gcgaggtatg
6121 taggcggtgc tacagagttc ttgaagtggt ggcctaacta cggctacact agaaggacag
6181 tatttggtat ctgcgctctg ctgaagccag ttaccttcgg aaaaagagtt ggtagctctt
6241 gatccggcaa acaaaccacc gctggtagcg gtggtttttt tgtttgcaag cagcagatta
6301 cgcgcagaaa aaaaggatct caagaagatc ctttgatctt ttctacgggg tctgacgctc
6361 agtggaacga aaactcacgt taagggattt tggtcatgag attatcaaaa aggatcttca
6421 cctagatcct tttaaattaa aaatgaagtt ttaaatcaat ctaaagtata tatgagtaaa
6481 cttggtctga cagttaccaa tgcttaatca gtgaggcacc tatctcagcg atctgtctat
```

*Fig.2B*

```
6541 ttcgttcatc catagttgcc tgactccccg tcgtgtagat aactacgata cgggagggct
6601 taccatctgg ccccagtgct gcaatgatac cgcgagaccc acgctcaccg gctccagatt
6661 tatcagcaat aaaccagcca gccggaaggg ccgagcgcag aagtggtcct gcaactttat
6721 ccgcctccat ccagtctatt aattgttgcc gggaagctag agtaagtagt tcgccagtta
6781 atagtttgcg caacgttgtt gccattgctg caggcatcgt ggtgtcacgc tcgtcgtttg
6841 gtatggcttc attcagctcc ggttcccaac gatcaaggcg agttacatga tcccccatgt
6901 tgtgcaaaaa agcggttagc tccttcggtc ctccgatcgt tgtcagaagt aagttggccg
6961 cagtgttatc actcatggtt atggcagcac tgcataattc tcttactgtc atgccatccg
7021 taagatgctt ttctgtgact ggtgagtact caaccaagtc attctgagaa tagtgtatgc
7081 ggcgaccgag ttgctcttgc ccggcgtcaa cacgggataa taccgcgcca catagcagaa
7141 ctttaaaagt gctcatcatt ggaaaacgtt cttcggggcg aaaactctca aggatcttac
7201 cgctgttgag atccagttcg atgtaaccca ctcgtgcacc caactgatct tcagcatctt
7261 ttactttcac cagcgtttct gggtgagcaa aaacaggaag gcaaaatgcc gcaaaaaagg
7321 gaataagggc gacacggaaa tgttgaatac tcatactctt ccttttttcaa tattattgaa
7381 gcatttatca gggttattgt ctcatgagcg gatacatatt tgaatgtatt tagaaaaata
7441 aacaaatagg ggttccgcgc acatttcccc gaaaagtgcc acctgacgtc taagaaacca
7501 ttattatcat gacattaacc tataaaaata ggcgtatcac gaggccctt cgtcttcaag
7561 aattcatacc agatcaccga aaactgtcct ccaaatgtgt ccccctcaca ctcccaaatt
7621 cgcgggcttc tgcctcttag accactctac cctattcccc acactcaccg gagccaaagc
7681 cgcggccctt ccgtttcttt gct
```

*Fig.2C*

ANTITUMOR VACCINATION USING ALLOGENEIC TUMOR CELLS EXPRESSING ALPHA (1,3)-GALACTOSYLTRANSFERASE

CROSS REFERENCE TO RELATED APPLICATION

This application is a continuation of U.S. application Ser. No. 11/013,685 (filed Dec. 16, 2004), which is a Continuation-in-Part of U.S. application Ser. No. 10/682,178 (filed Oct. 9, 2003), which is a nonprovisional application of Provisional Application No. 60/417,343, filed Oct. 9, 2002, which applications are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NEWL_014_05US_Seqlist.txt, date recorded: Dec. 16, 2010, file size 11 kilobytes).

FIELD OF THE INVENTION

The present invention relates to methods and compositions for treating cancer by stimulating humoral and cellular immune responses against tumor cells. In particular, this invention is directed to methods for stimulating complement-mediated destruction of tumors cells and concomitant stimulation of tumor specific antibody production and tumor specific cytotoxic cells.

BACKGROUND OF THE INVENTION

A primary barrier to xenotransplantation has been the essentially immediate recognition of carbohydrate epitopes present in the foreign tissue causing hyperacute xenograft rejection (HAR). The reaction begins immediately upon reperfusion, and once initiated destroys the foreign tissue within minutes to a few hours. The presence of HAR in some donor/recipient combinations while not others is postulated to be related to two primary factors, a) the binding of xenoreactive natural antibodies of the recipient to antigens or endothelial cells in the graft and b) the incompatibility of complement regulatory proteins in the transplant with the complement system of the recipient, allowing uncontrolled activation of complement. Greater than 1% of the complement-fixing natural antibodies in human serum recognize a single structure-Galα(1-3)Galβ(1,4)GlcNAc-R. The synthesis of Galα(1-3)Galβ(1,4)GlcNAc-R is catalyzed by the enzyme α(1,3) galactosyltransferase (αGT.

This enzyme catalyzes the synthesis of α-galactosyl (αGal) epitopes in the Golgi apparatus of cells from various non-primate mammals by the following reaction:

This enzyme was found to be active in new world monkeys but not in old world monkeys and humans. The αGT cDNA has been cloned from bovine and murine cDNA libraries. Larson, R. D. et al. (1989) "Isolation of a cDNA Encoding Murine UDP galactose; .β-D-galactosyl-(1,4)-N Acetyl-D-Glucosamine α-(1,3) Galactosyl Transferase: Expression Cloning by Gene Transfer", PNAS, USA 86:8227; and Joziasse, D. H. et al., (1989) "Bovine α-(1,3) Galactosyl Transferase: Isolation and Characterization of a cDNA Clone, Identification of Homologous Sequences in Human Genomic DNA", J. Biol Chem 264:14290.

The gene is present in the human genome, although no transcription has been detected. Instead, two frame shift mutations were found (deletions generating premature stop codons) in the human exons encoding the enzyme. See generally, Galili, Uri "Evolution in Pathophysiology of the Human Natural anti-α-Galactosyl IgG (anti-αGal) Antibody", Springer Semin. Immunopathol. (1993) 15:155-171.

anti-αGal, a naturally occurring antibody present in all humans, specifically interacts with the carbohydrate epitope Galα(1-3)Galβ(1,4)GlcNAc-R (αGal epitope). This antibody does not interact with any other known carbohydrate epitope produced by mammalian cells (Galili, 1993, Springer Seminar Immunopathology 15:153). anti-αGal constitutes approximately 1% of circulating IgG (Galili et al., 1984, J. Exp. Med. 160:1519) and is also found in the form of IgA and IgM (Davine et al., 1987, Kidney Int. 31:1132; Sandrin et al., 1993, Proc. Natl. Acad. Sci. USA 90:11391). It is produced by 1% of circulating B lymphocytes (Galili et al., 1993, Blood 82:2485). Production of this natural anti-αGal Ab in humans is constantly stimulated by the presence of αGal carbohydrate residues present in intestinal and pulmonary bacterial flora. In humans anti-αGal reacts to the presence of this epitope in hyperacute xenograft rejection and complement is swift and certain resulting in destruction of foreign tissues in minutes to hours.

It is an object of this invention to develop a therapeutic cancer vaccine by introducing the gene encoding for αGT into tumor cells, to drive the addition of αGal epitopes to such vaccine tumor cells in order to allow for enhanced opsonization of the vaccine cells by natural anti-αGal antibodies and stimulate tumor antigen presentation to induce a humoral and cellular immune response to the tumor specific antigens.

It is a further object of this invention to provide a therapeutic pharmaceutical composition comprising recombinant tumor cells which express and process αGT to engineer αGal epitopes on cells.

It is a further object of the invention to provide compositions and methods for treatment of tumors, viruses, neoplastic cells or other cells, which grow and evade the cellular and humoral immune response.

Other objects of the invention will become apparent from the description of the invention which follows.

SUMMARY OF THE INVENTION

This invention relates to methods and compositions for causing an immune response to selectively targeting and killing of tumor cells. Through ex vivo gene therapy protocols tumor cells are engineered to express an αGal epitope. The cells are then killed (by gamma or ultraviolet irradiation, heat, formaldehyde and the like) and administered to a patient. The αGal epitope causes opsonization of the tumor cell which enhances tumor specific antigen presentation of antigens present in the entire tumor cell. An important feature of the invention contemplates the use of whole cells in the pharmaceutical compositions of the invention. This provides for processing of tumor associated antigens present within the entire tumor cell regardless of whether those proteins have been affected by the addition of αGal epitopes or not. Since αGal modifications affect multiple glycoproteins and glycolipids on the cell surface, the animal's immune system will have an increased opportunity to detect, process and generate antibodies and a cellular immune response to tumor specific antigens. The animal's immune system thus is stimulated to produce tumor specific antibodies and immune cells, which will attack and kill αGal negative tumor cells present in the animal that bear tumor associated antigens which are common with the ones provided by the engineered whole cell vaccine.

According to the invention a pharmaceutical composition is generated by introducing a polynucleotide sequence, which encodes upon expression the murine αGT to whole tumor cells ex vivo. The recipient tumor cells may be syngenic, allogenic, or autologous. The sequence is introduced through any nucleotide transfer vehicle which can comprise a viral or non-viral vector, a plasmid or vector producer cells which produce active viral particles. These gene transfer vehicles transform the tumor cells, and cause expression of foreign genetic material inserted therein. The resulting gene product catalyzes the synthesis of αGal epitope, on cell surface glycoproteins and glycolipids present on said cells. The invention contemplates the use of whole tumor cells with multiple cell surface glycoproteins to maximize the binding of αGal epitopes by pre-existing anti-αGal antibodies thus enhancing binding of this complexes to the Fc receptors present on antigen presenting cells and thus triggering antigen presentation of a plurality of tumor associated antigens present in said vaccine tumor cell. In a more preferred embodiment multiple types of transformed cells may be administered from the same tissue type, or cancer type thus further increasing the number of different epitopes provided to increase the probability of complete amelioration of tumor cells present in the individual.

The invention comprises a pharmaceutical composition and a method for making the same which includes a therapeutically effective amount of a mixture of attenuated tumor cells said mixture comprising a plurality of cell surface glycoproteins which include an αGal epitope and a carrier. In a preferred embodiment the cells are whole cells. Methods for making the compositions include obtaining a collection of live tumor cells, transforming said cells with a nucleotide sequence that encodes upon expression a an αGT so that an αGal epitope is presented on cell surface glycoproteins of said cells. The cells are then killed and combined with a pharmaceutical carrier for administration.

DEFINITIONS

Various terms relating to the compositions and methods of the present invention are used herein above and also throughout the specification and claims.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

The term "α-(1,3) Galactosyl Transferase encoding sequence", or "αGT encoding sequence" is meant any polynucleotide sequence which encodes a protein that forms α-galactosyl (αGal) epitopes by the following reaction:

Galβ(1,4)GlcNAc-R+UDP-Gal→Galα(1-3)Galβ(1,4) GlcNAc-R

This can include variants, modifications, truncations and the like as well as murine sequences, bovine or sequences from any other source known to those of skill in the art and available in Genbank, other publications or databases which retain the function of the aforementioned reaction.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "animal" as used herein should be construed to include all anti-αGal synthesizing animals including those which are not yet known to synthesize anti-αGal. For example, some animals such as those of the avian species, are known not to synthesize αGal epitopes. Due to the unique reciprocal relationship among animals which synthesize either anti-αGal or αGal epitopes, it is believed that many animals heretofore untested in which αGal epitopes are absent may prove to be anti-αGal synthesizing animals. The invention also encompasses these animals.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "anti-αGal" includes any type or subtype of immunoglobulin recognizing the αGal epitope, such as IgG, IgA, IgE or IgM anti-αGal antibody.

As used herein, the term "antigen" is meant any biological molecule (proteins, peptides, lipids, glycans, glycoproteins, glycolipids, etc) that is capable of eliciting an immune response against itself or portions thereof, including but not limited to, tumor associated antigens and viral, bacterial, parasitic and fungal antigens.

As used herein, the term "antigen presentation" is meant the biological mechanism by which macrophages, dendritic cells, B cells and other types of antigen presenting cells process internal or external antigens into subfragments of those molecules and present them complexed with class I or class II major histocompatibility complex or CD1 molecules on the surface of the cell. This process leads to growth stimulation of other types of cells of the immune system (such as CD4+, CD8+, B and NK cells), which are able to specifically recognize those complexes and mediate an immune response against those antigens or cells displaying those antigens.

The term "conservatively modified variants" applies to both amino acid and nucleic acid sequences and is intended to be included whenever a reference to a specific sequence is made. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).
See also, Creighton (1984) Proteins W.H. Freeman and Company.

We define the "percentage of sequence identity" of two aminoacid sequences as the number of identical aminoacids shared by these two aminoacid sequences after a pairwise alignment divided by the total length of the shortest sequence of the pair.

We define the "percentage of sequence similarity" of two aminoacid sequences as the number of identical aminoacids plus conservative aminoacid substitutions shared by these two sequences after a pairwise alignment, divided by the total length of the shortest sequence of the pair.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

When the nucleic acid is prepared or altered synthetically, advantage can be taken of known codon preferences of the intended host where the nucleic acid is to be expressed.

With respect to proteins or peptides, the term "isolated protein (or peptide)" or "isolated and purified protein (or peptide)" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eukaryote. An "isolated nucleic acid molecule" may also comprise a cDNA molecule. With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, insect, amphibian, or mammalian cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "opsonization" of an antigen or a tumor cell is meant binding of the anti-αGal epitopes present in the antigen or on the surface of a tumor cell by anti-αGal antibodies thereby enhancing phagocytosis of the opsonized antigen or tumor cell by macrophages, dendritic cells, B cells or other types of antigen presenting cells through binding of the Fc portion of the antibodies to the Fc receptors present on the surface of antigen presenting cells.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

With respect to antibodies, the term "immunologically specific" refers to antibodies that bind to one or more epitopes of a protein of interest, but which do not substantially recognize and bind other molecules in a sample containing a mixed population of antigenic biological molecules.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "therapeutically effective amount" is meant an amount of treatment composition sufficient to elicit a measurable decrease in the number, quality or replication of previously existing tumor cells as measurable by techniques including but not limited to those described herein.

The term "tumor cell" is meant a cell which is a component of a tumor in an animal, or a cell which is determined to be destined to become a component of a tumor, i.e., a cell which is a component of a precancerous lesion in an animal. Included within this definition are malignant cells of the hematopoietic system which do not form solid tumors such as leukemias, lymphomas and myelomas.

The term "tumor" is defined as one or more tumor cells capable of forming an invasive mass that can progressively displace or destroy normal tissues.

The term "malignant tumor" are those tumors formed by tumor cells that can develop the property of dissemination beyond their original site of occurrence.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "clone" is a population of cells derived from a single cell or common ancestor by mitosis. A "cell line" is a clone of a primary cell that is capable of stable growth in vitro for many generations.

The term "treat" or "treating" with respect to tumor cells refers to stopping the progression of said cells, slowing down growth, inducing regression, or amelioration of symptoms associated with the presence of said cells.

The term "xenogeneic cell" refers to a cell that derives from a different animal species than the animal species that becomes the recipient animal host in a transplantation or vaccination procedure.

The term "allogeneic cell" refers to a cell that is of the same animal species but genetically different in one or more genetic loci as the animal that becomes the "recipient host". This usually applies to cells transplanted from one animal to another non-identical animal of the same species.

The term "syngeneic cell" refers to a cell which is of the same animal species and has the same genetic composition for most genotypic and phenotypic markers as the animal who becomes the recipient host of that cell line in a transplantation or vaccination procedure. This usually applies to cells transplanted from identical twins or may be applied to cells transplanted between highly inbred animals.

DESCRIPTION OF THE FIGURES

FIG. 2, SEQ ID NO:1, is the sequence of the pLNC-KG plasmid depicted in FIG. 1.

Figure 10:
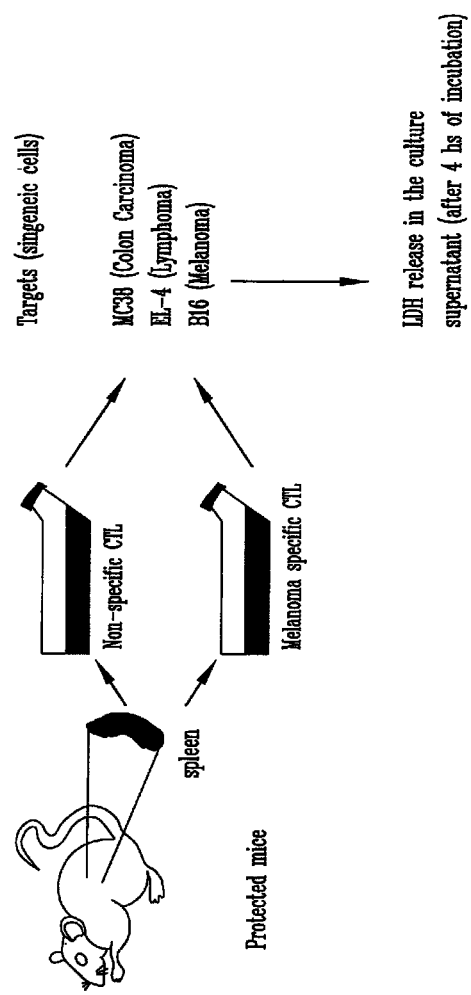
FIG. 10 is a schematic showing induction of melanoma specific cytotoxic T cells in mice that survived a lethal dose injection of non-irradiated $\alpha Gal^{(+)}$ cells. Splenocytes from two mice that survived the first challenge with $\alpha Gal^{(+)}$ B16 cells from FIG. 7, were used to generate Cytotoxic T Lymphocytes (CTL) in vitro. Splenocytes were harvested 90 days after the injection of αGal$^{(+)}$ B16 from tumor free mice and melanoma specific cultures were generated by culturing splenocytes with irradiated αGal$^{(-)}$ B16 cells during 5 days in the absence of IL-2. CTL were harvested and tested against the specific target αGal$^{(-)}$ B16 and the non-specific syngeneic cell lines colon carcinoma MC38 and T cell lymphoma EL-4. Specific cytotoxicity was determined after 4 h of incubation of CTL with specific and non-specific targets by measuring LDH release in the culture supernatant.
Figure 11:
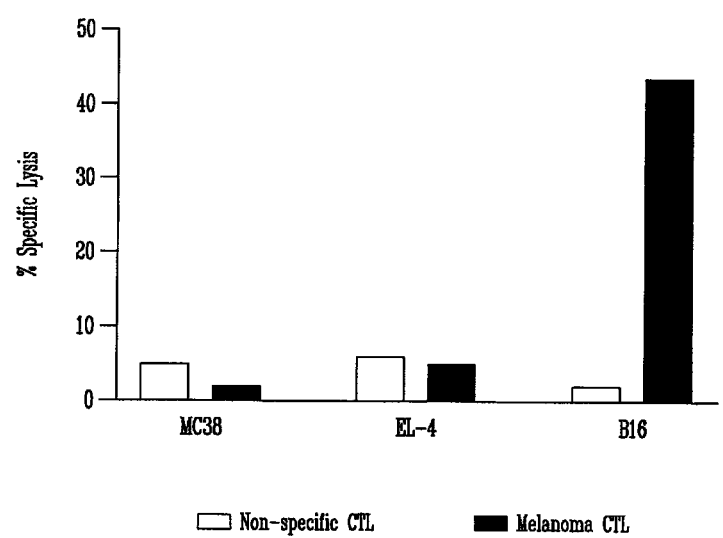

FIG. 11 is a graph showing the results of induction of B16 melanoma-specific cytotoxic T cells in mice that survived a lethal dose injection of non-irradiated αGal$^{(+)}$ cells as depicted in FIG. 10.

Figure 12:
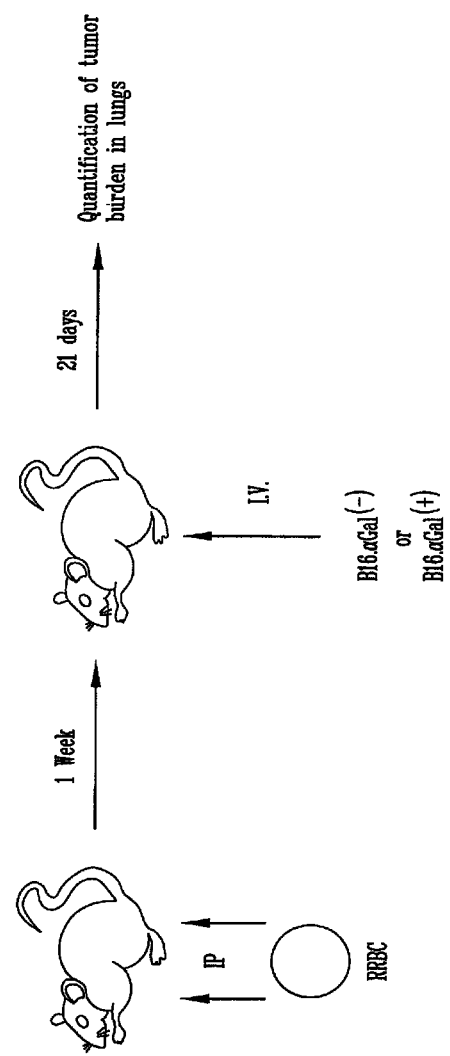

FIG. 12 is a schematic showing the experimental design of disseminated melanoma metastasis model in the αGT knockout mice by intravenous injection of a lethal close of non-irradiated αGal$^{(+)}$ or αGal$^{(-)}$ B16 melanoma cells. Females and males αGT KO mice were immunized with RRBC to increase the anti-αGal Ab titers as in FIG. 3. One week after the last immunization, mice were intravenously injected with αGal$^{(-)}$ B16 or αGal$^{(+)}$ B16 in the tail vein. Three weeks after the injection, lungs were harvested and lung melanoma metastases were enumerated.

Figure 13:
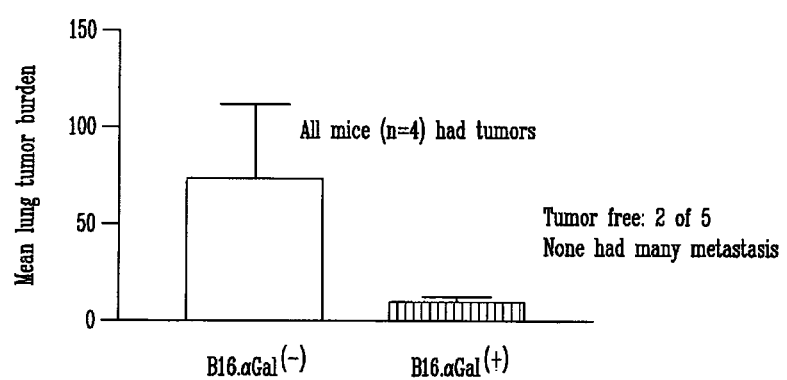

FIG. 13 is a graph showing the statistical results of the experiment in FIG. 12.

Figure 14:
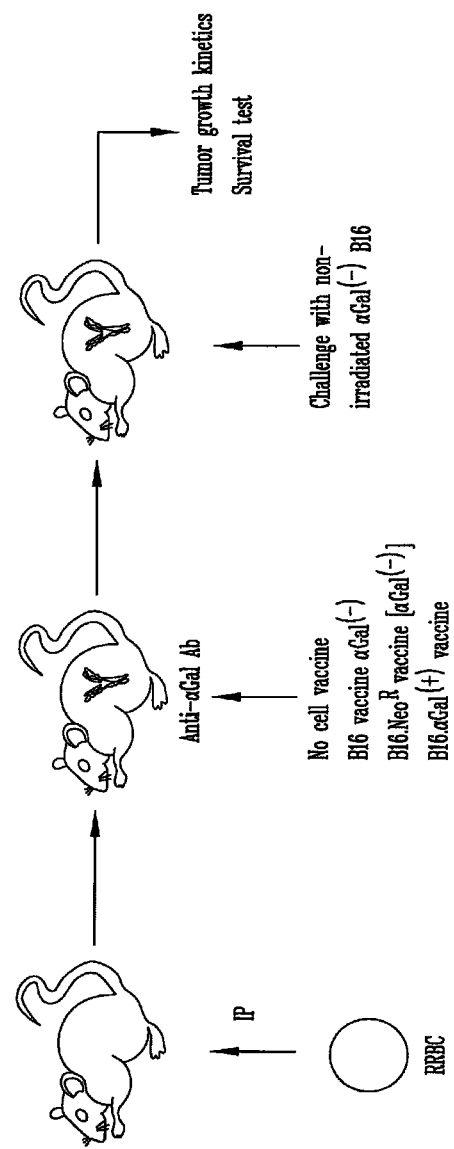

FIG. 14 is a schematic showing the experimental design for prevention of subcutaneous αGal$^{(-)}$ melanoma tumor development in αGT knockout mice after vaccination with irradiated αGal$^{(+)}$ B16 melanoma cells. Cell vaccines were prepared using the B16-derived cell lines described in previous experiments, which are: native αGal$^{(-)}$ B16, αGal$^{(-)}$ B16.LNL transduced with control vector and αGal$^{(+)}$ B16 cells transduced with the vector encoding the murine αGT gene. Cell vaccines were prepared by γ-irradiation (250 Gy) to prevent cell proliferation and stored in freezing media until use. Before injection cell vaccines were thawed, washed counted and injected subcutaneously suspended in Hanks' Balanced Salt Solution (HBSS). All αGT KO mice used were injected with RRBC as in FIG. 3. One week after the last RRBC injection, mice received the first close of cell vaccine. Two weeks later the cell vaccination was repeated. The dose of each vaccine was $10^6$ cells per mouse administered subcutaneous. Two weeks after the last cell vaccines, mice were injected subcutaneous with $10^5$ non-irradiated native αGal$^{(-)}$ B16 cells and observed for tumor development twice a week during 90 days.

Figure 15:
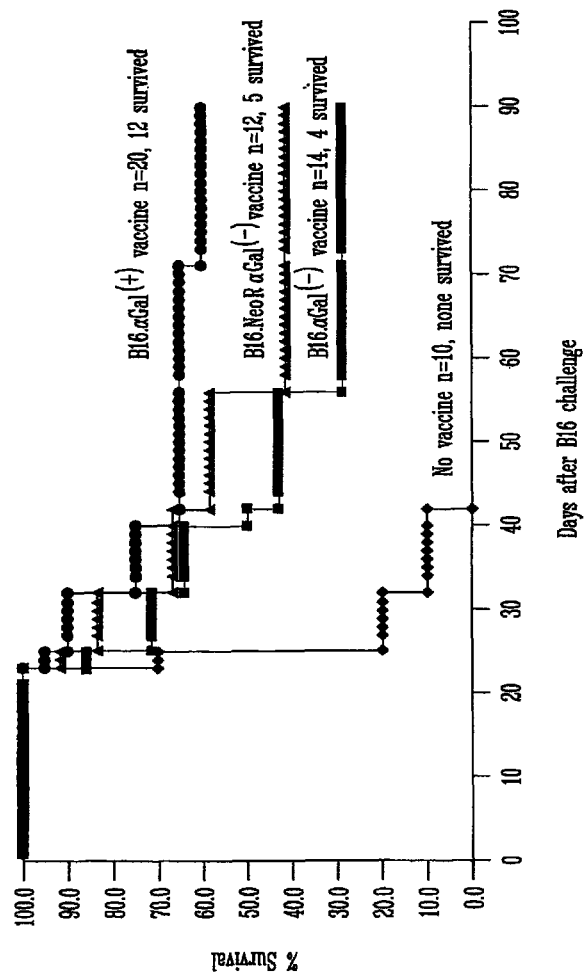

FIG. 15 is a graph depicting the Kaplan-Meier survival analysis of the experiment described in FIG. 14.

Figure 16:
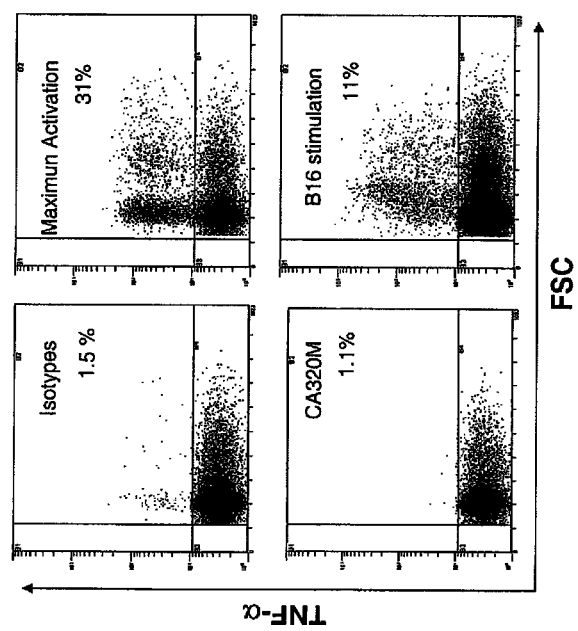

FIG. 16 shows the results of FACS analysis of recognition of TNF-α. Detection of intracellular TNF-α by melanoma specific T cells induced in mice vaccinated with irradiated αGal$^{(+)}$ B16 cells after in vitro recognition of αGal$^{(-)}$ B16 melanoma cells. Splenocytes from tumor free mice were harvested from mice vaccinated with αGal$^{(+)}$ B16 vaccines 90 days after the injection of αGal$^{(-)}$ B16 melanoma (mice that survived from FIG. 15). To measure in vitro recognition of αGal$^{(-)}$ B16 intracellular TNF-α was detected by FACS. T cells were cultured for 6 h in presence or absence of stimulation with Brefeldin A to block secretion of cytokines. For maximum activation PMA/Ca$^{++}$ Ionophore was used. Cells were cultured with $10^5$ irradiated B16 to measure specific recognition or with $10^5$ CA320M as non-melanoma syngeneic negative control cell line. After incubation cells were harvested, permeabilized fixed and stained for intracellular TNF-α using PE-labeled anti-TNF-α monoclonal Ab. Cells were analyzed using Coulter Flow cytometer, acquiring at least 10.000 gated lymphocytes.

Figure 17:
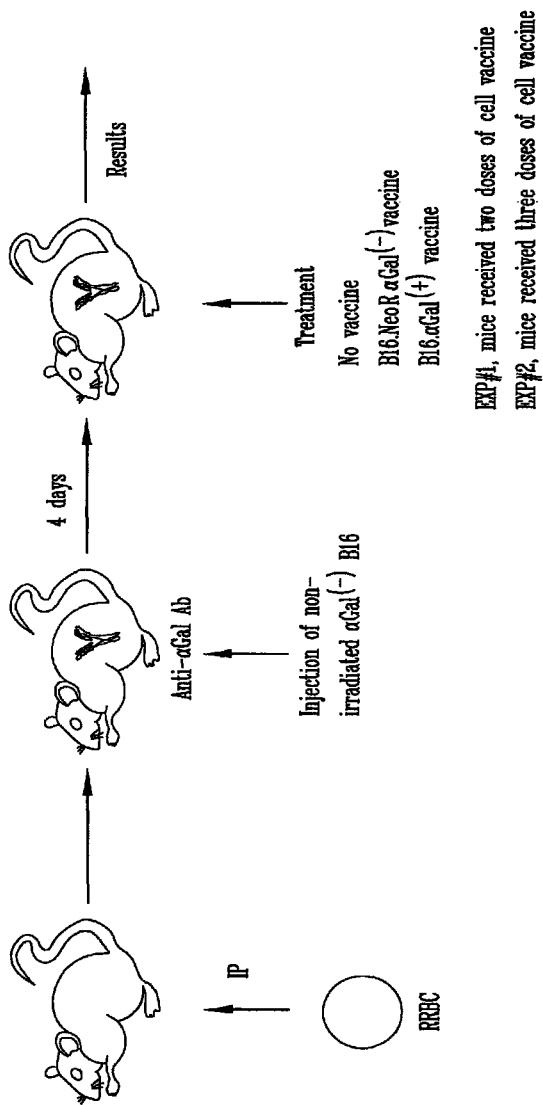

FIG. 17 is a schematic showing the experimental design for therapeutic treatment of pre-established subcutaneous tumors through vaccination with irradiated melanoma cells. Therapeutic treatment of pre-established subcutaneous αGal$^{(-)}$ melanoma tumors through vaccination with irradiated αGal$^{(+)}$ or αGal$^{(-)}$ B16 melanoma cells. Mice were injected with RRBC as explained in FIG. 3. One week after the last RRBC injection, mice were subcutaneously injected with $10^5$ non-irradiated αGal$^{(-)}$ B16 melanoma cells and randomized. In Experiment #1, two doses of cell vaccines were administered at 3 and 6 days after subcutaneous injection of αGal$^{(-)}$ B16. In Experiment #2 mice received three doses of the irradiated cell vaccines at 4, 11 and 18 days after the subcutaneous injection with live αGal$^{(-)}$ B16 cells. In these experiments, two cell vaccines were used: irradiated αGal$^{(-)}$ B16 transduced with control vector or irradiated αGal$^{(+)}$ B16 cells.

Figure 18A:
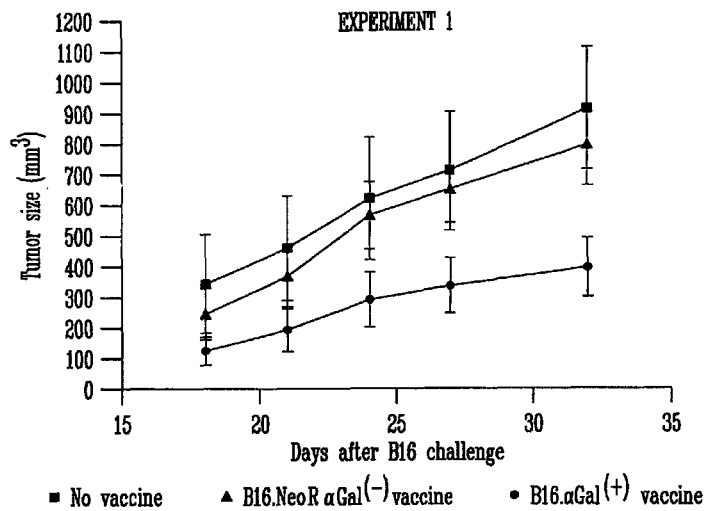
Figure 18B:
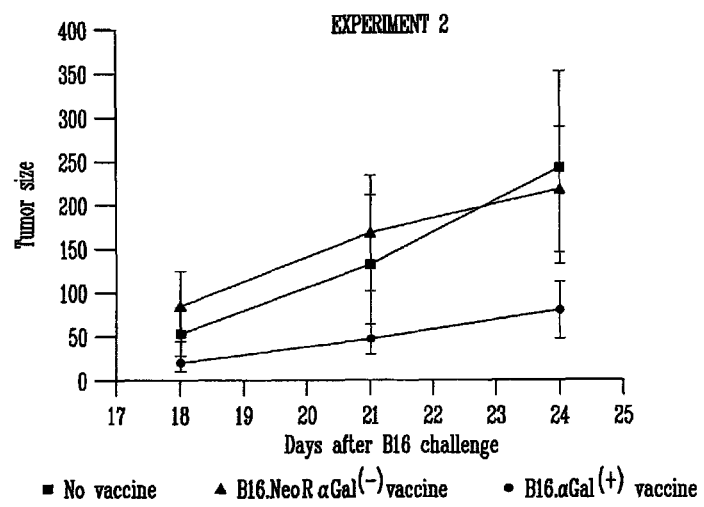

FIGS. 18a and 18b show graphs of results of two different experiments of tumor growth kinetics in mice with pre-established subcutaneous αGal$^{(-)}$ melanoma tumors receiving vaccination with irradiated αGal$^{(+)}$ or αGal$^{(-)}$ B16 melanoma cells. Tumor sizes were measured at early time points in mice receiving or not cell vaccines. The values represent the mean of tumor size of all mice in each group.

Figure 19:
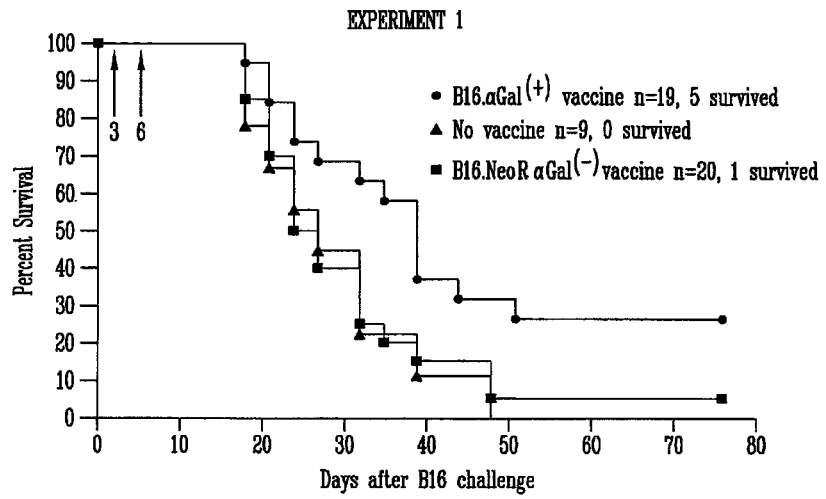

FIG. 19 is a graph showing Kaplan-Meier survival analysis of mice with pre-established subcutaneous αGal$^{(-)}$ B16 melanoma tumors that received therapeutic vaccination with irradiated αGal$^{(+)}$ or αGal$^{(-)}$ B16 melanoma cells. Mice injected with αGal$^{(-)}$ B16 and treated or not with αGal$^{(+)}$ or αGal$^{(-)}$ B16 melanoma vaccines were evaluated for survival during 75 days (EXP #1).

Figure 20:
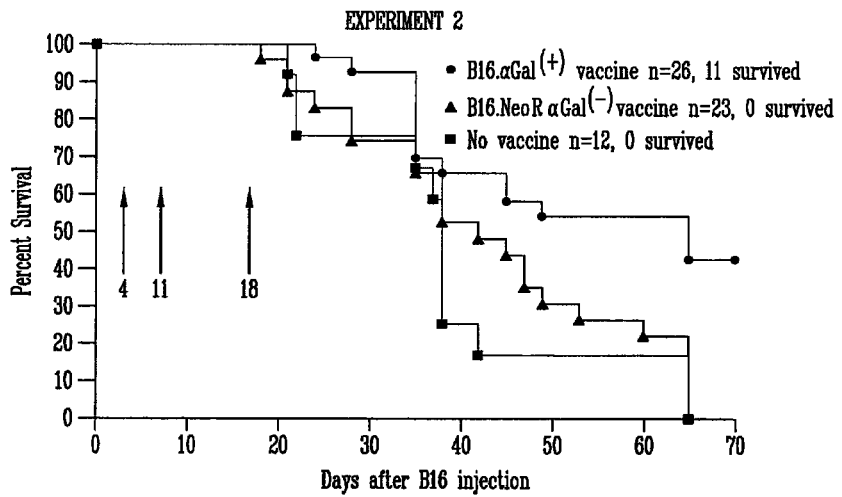

FIG. 20 is a graph showing Kaplan-Meier survival analysis of mice with pre-established subcutaneous αGal$^{(-)}$ B16 melanoma tumors that received therapeutic vaccination with irradiated αGal$^{(+)}$ or αGal$^{(-)}$ B16 melanoma cells. Mice injected with αGal$^{(-)}$ B16 and treated or not with αGal$^{(+)}$ or αGal$^{(-)}$ B16 melanoma vaccines were evaluated for survival during 70 days (EXP#2).

Figure 21:
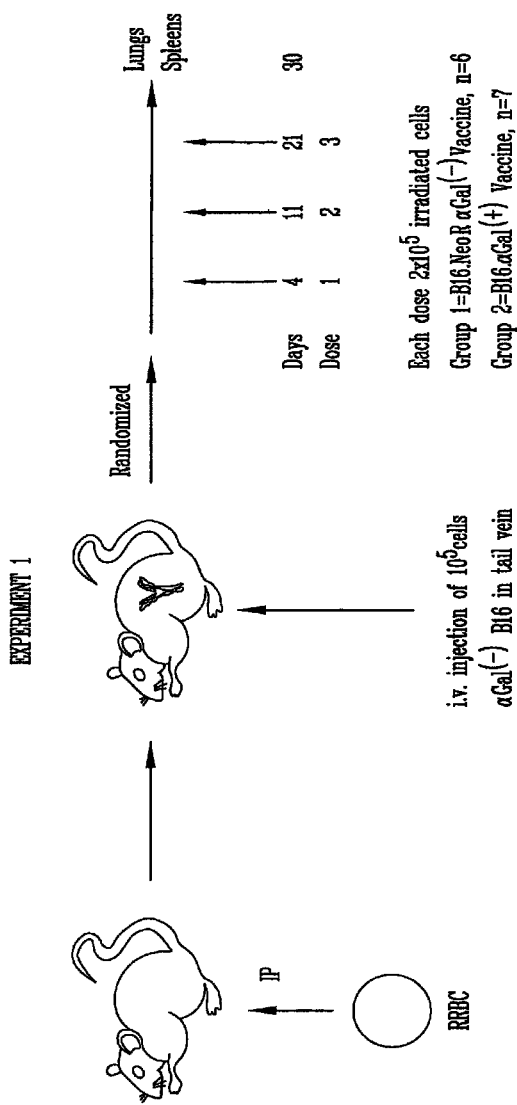

FIG. 21 is a diagram showing the experimental design for therapeutic treatment of pre-established lung metastatic tumors. Treatment of pre-established disseminated lung metastatic αGal$^{(-)}$ melanoma tumors through vaccination with irradiated αGal$^{(+)}$ or αGal$^{(-)}$ B16 melanoma cells. Mice were injected with RRBC as explained in FIG. 3. One week after the last RRBC injection, mice were intravenously (i.v.) injected with non-irradiated αGal$^{(-)}$ B16 melanoma cells and randomized. They were subsequently vaccinated with either αGal$^{(-)}$ B16 or αGal$^{(+)}$ B16 vaccine cells at days 4, 11 and 21 after establishment of the disseminated metastases. At day 30 animals were sacrificed and their lung tumor burden was evaluated.

Figure 22:
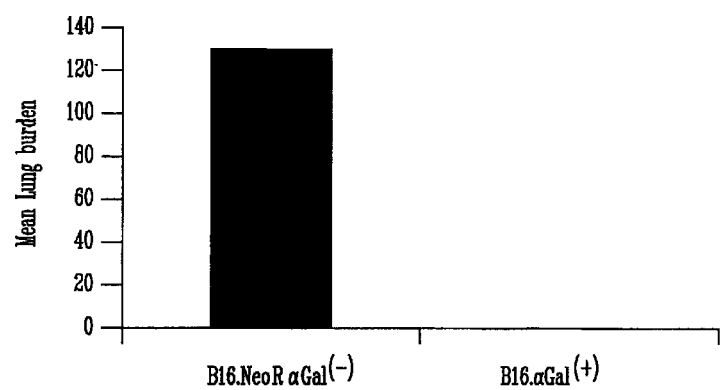

FIG. 22 is a graph showing tumor burden in experiment 1 of the protocol shown in FIG. 21. In experiment #1 mice received $10^5$ αGal$^{(-)}$ B16 melanoma cells. Thirty days after the i.v injection of non-irradiated melanoma cells, mice were sacrificed and the lung melanoma metastases were enumerated.

Figure 23:
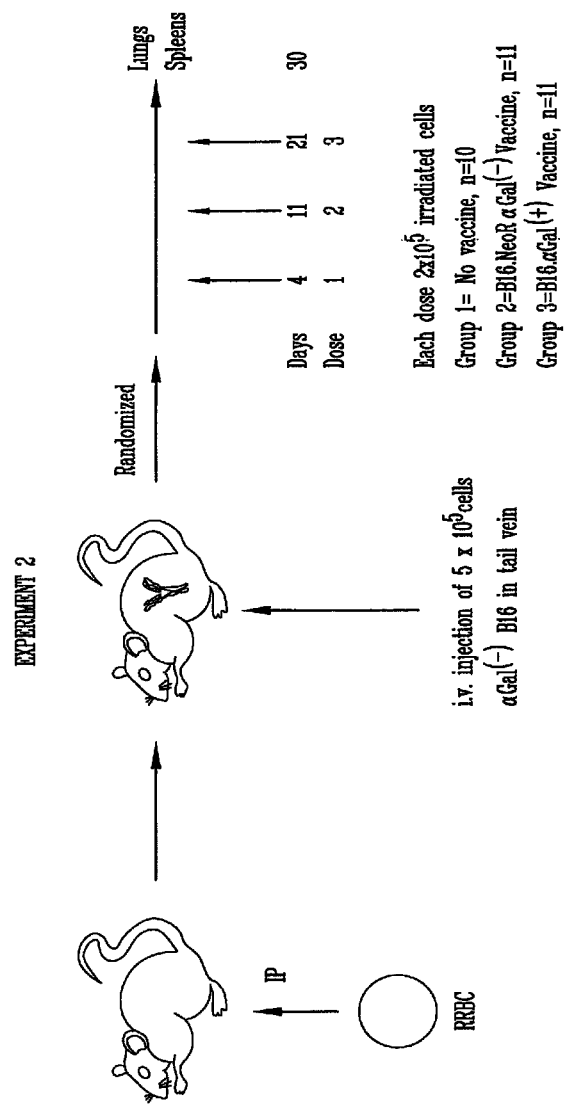

FIG. 23 is a diagram showing a second experimental design for therapeutic treatment of pre-established disseminated metastatic melanoma tumors. In experiment #2 mice received $5\times10^5$ αGal$^{(-)}$ B16 melanoma cells. After this, mice were treated subcutaneous with melanoma cell vaccines. They received three doses of $2\times10^5$ irradiated αGal$^{(-)}$ B16 transduced with control vector or irradiated αGal$^{(+)}$ B16 cells on days 4, 11 and 21 after the i.v injection of non-irradiated αGal$^{(-)}$ B16.

Figure 24A:
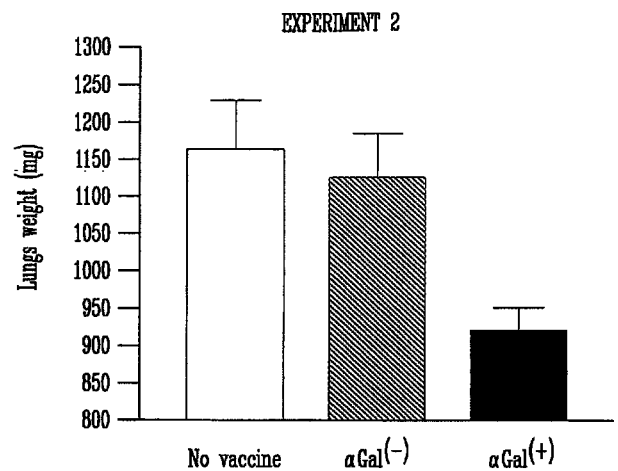
Figure 24B:
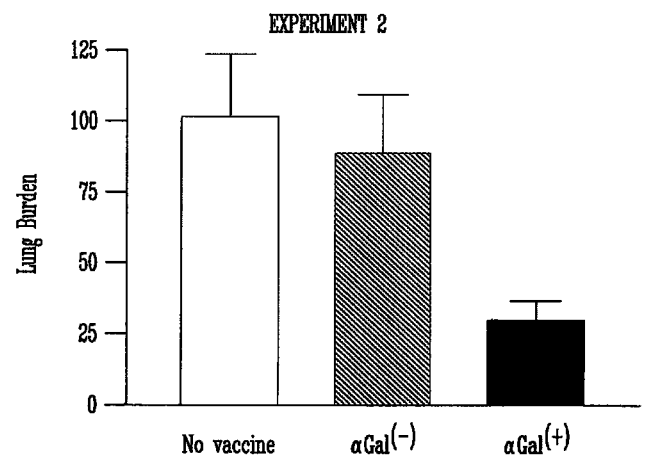

FIGS. 24a and 24b are graphs showing the results of the experiment described in FIG. 23 expressed as average weight of the lungs (24A) or as the mean lung tumor burden (24B).

Figure 25:
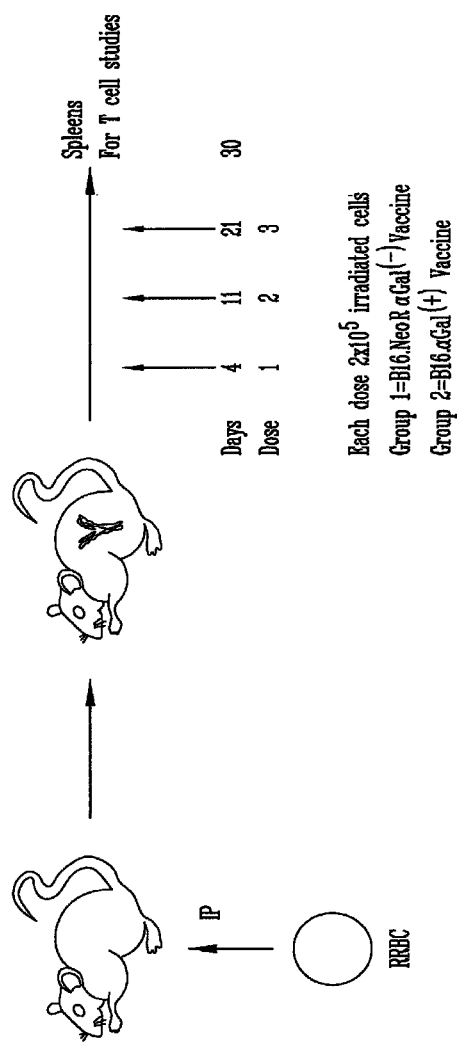

FIG. 25 is a diagram showing the experimental design to demonstrate in vitro induction of T cell immunity specific for αGal$^{(-)}$ B16 melanoma after vaccination with αGal$^{(+)}$ or αGal$^{(-)}$ B16 cells. Mice were injected with RRBC as in FIG. 3. Two weeks after the last RRBC injection mice received three subcutaneous injections of 2×10$^5$ irradiated αGal$^{(-)}$ B16 cells transduced with control vector or irradiated αGal$^{(+)}$ B16 cell vaccines. Two weeks after the last cell vaccine, splenocytes were harvested and T cell studies were performed. To determine specific recognition of αGal$^{(-)}$ B16, intracellular TNF-α and up-regulation of activation markers CD25 and CD69 were measured.

Figure 26:
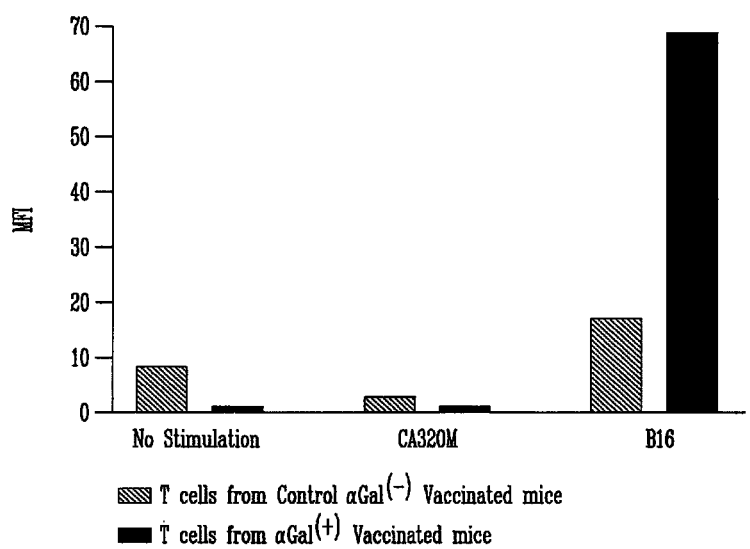

FIG. 26 is a graph showing the specific induction of TNF-α in T cell precursors of vaccinated animals that specifically recognize B16 antigens (FIG. 25). To detect TNF-α T cells were cultured for 6 h in presence or absence of stimulation with Brefeldin A to block secretion of cytokines. For maximum stimulation PMA/Ca$^{++}$ Ionophore was used as positive control. Cells were cultured with αGal$^{(-)}$ B16 to measure specific recognition or with CA320M, a non-melanoma syngeneic (H-2 b/b) small intestine cell line as negative control. After incubation cells were harvested, and stained for intracellular TNF-α. Positive cells were detected by FACS gating in lymphocytes in the Forward Scatter plot after acquisition of at least 10.000 gated events. The plot depicts the Mean Fluorescence Intensity (MFI) of TNF-α$^{(+)}$ cells.

Figure 27A:
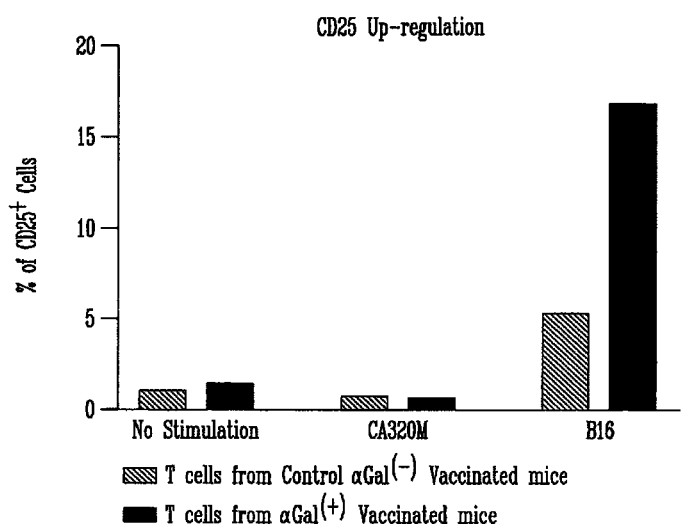
Figure 27B:
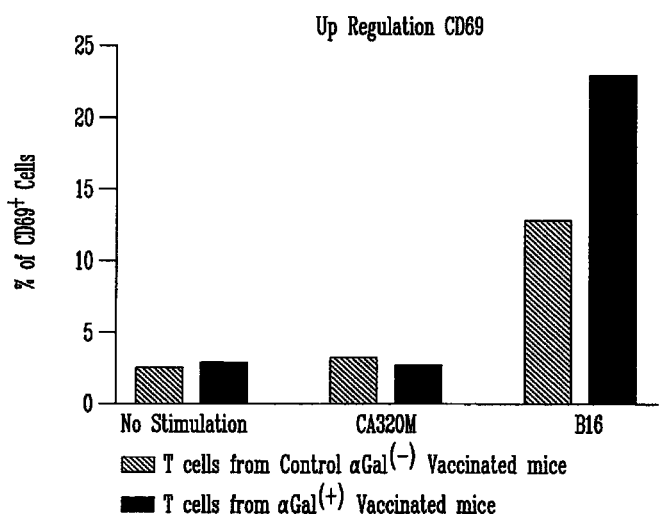

FIGS. 27a and 27b are graphs showing up-regulation of activation markers CD25 and CD69 in T cell precursors from animals vaccinated with αGal(+) cells, that specifically recognize B16 antigens. Measurements were performed after one day of culture under similar conditions as described in FIG. 26, in absence of Brefeldin A. After incubation cells were harvested and stained with PE-labeled monoclonal Ab anti-CD25 or anti-CD69. Acquisition was performed using Coulter Flow cytometer. The plots depict percentage of positive CD25 or CD69 cells.

Figure 28:
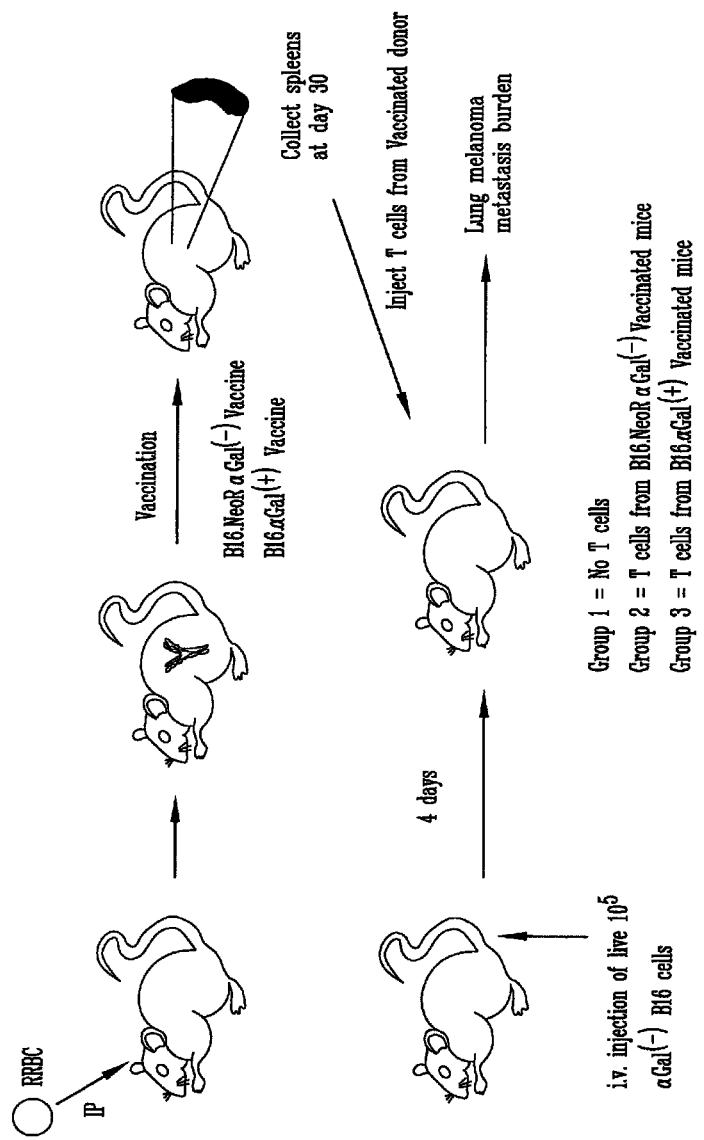

FIG. 28 shows a schematic of an In vivo demonstration of specific T cell mediated immunity with therapeutic effect against pre-established disseminated metastasis of αGal$^{(-)}$ B16 melanoma by adoptive T cell transfer from donor mice vaccinated with irradiated αGal$^{(+)}$ or αGal$^{(-)}$ B16 cells. Donor mice were injected with RRBC as in FIG. 3. Two weeks after the last RRBC injection mice received three subcutaneous injection of 2×10$^5$ irradiated αGal$^{(-)}$ B16 transduced with control vector or irradiated αGal$^{(+)}$ B16 cells vaccines. Two weeks after the last cell vaccine, splenocytes were harvested and transferred to sex-matched recipients. Four days previous to cell transfer, recipients were injected i.v. with non-irradiated αGal$^{(-)}$ B16 to establish the lung melanoma metastasis and randomized. Thirty days after T cell transfer, recipients were euthanized and lung melanoma metastasis burden determined by weighting the lungs and by enumerating melanoma tumors.

Figure 29A:
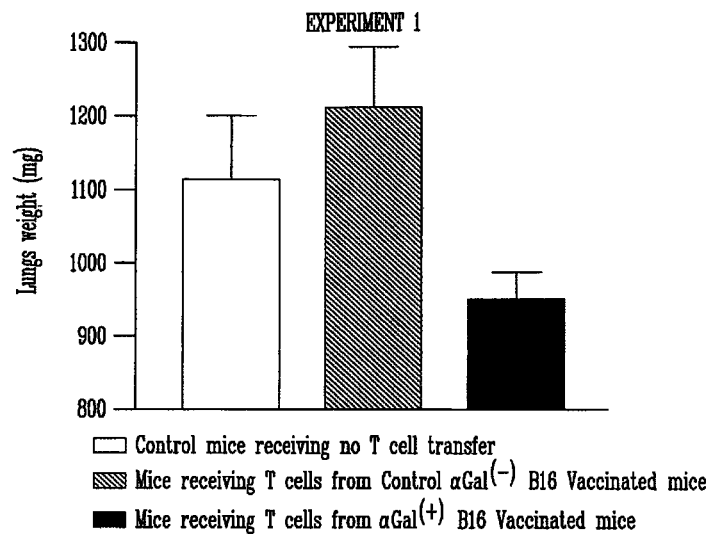
Figure 29B:
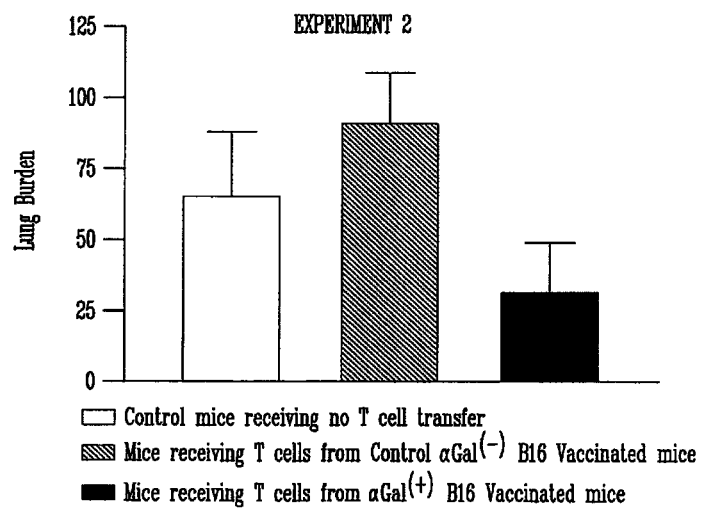

FIGS. 29a and 29b are graphs which depict the results of the experiment described in FIG. 28. Bars represent the mean and error bars, the SEM. Two independent experiments were performed and they are shown.

Figure 30:
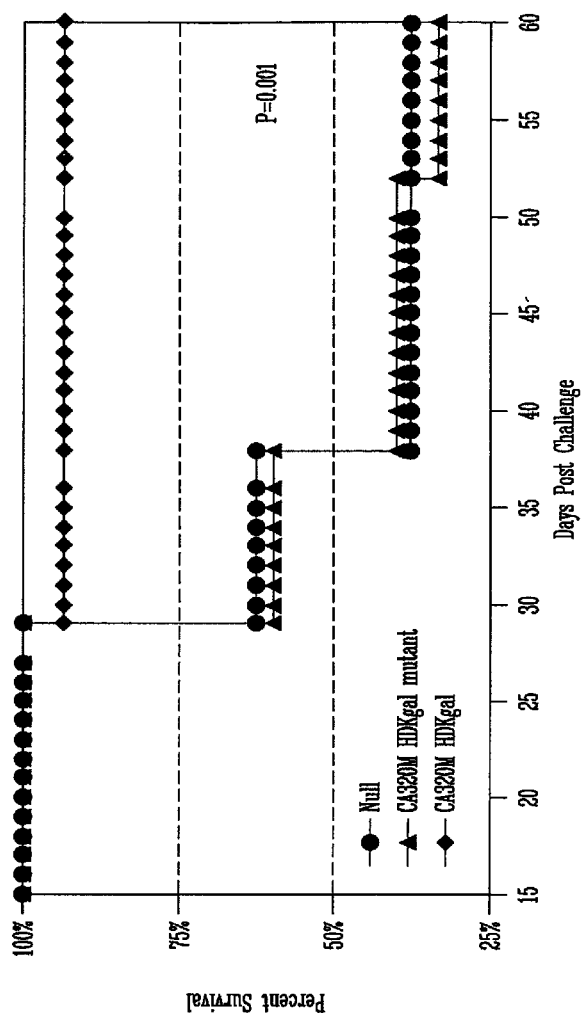

FIG. 30 is a graph showing survival analysis of αGT KO mice vaccinated with αGal$^{(+)}$ or αGal$^{(-)}$ irradiated CA320M sarcoma cells after subcutaneous injection of a lethal dose of non-irradiated αGal$^{(-)}$ CA320M sarcoma cells. Mice were injected with RRBC as in FIG. 3. Two weeks after the last RRBC injection they were vaccinated subcutaneous with either 1×10$^3$ CA320M transduced with 10 MOI HDKgalΔsalI [αGal$^{(-)}$ vector] or HDKgal1 [αGal$^{(-)}$ vector] followed by 25 Gy irradiation. Twenty-one days later mice were injected subcutaneous with 1×10$^7$ non-irradiated CA320M cells. Null consisted of no vaccine. Survival analysis was performed during a period of observation of 60 days.

DETAILED DESCRIPTION OF THE INVENTION

The basic rationale for immune therapy against tumors is the induction of an effective immune response against tumor-associated antigens (TAA), which in turn results in immune-mediated destruction of proliferating tumor cells expressing these antigens. For an immune response to be effective against TAAs comprising protein, these antigens must first be endocytosed by antigen presenting cells (APC) such as macrophages, dendritic cells and B cells. Within APCs, TAAs are degraded in the lysosomal compartment and the resulting peptides are expressed on the surface of the macrophage cell membrane mostly in association with MHC Class II molecules but also in association with MHC class I molecules. This expression mediates recognition by specific CD4$^+$ helper T cells and subsequent activation of these cells to effect the immune response (Stevenson, 1991, FASEB J. 5:2250; Lanzavecchia, 1993, Science 260:937; Pardoll, 1993, Immunol. Today 14:310). The majority of human TAA molecules have not been defined in molecular terms, preventing these for use as targets for drug therapy or as anti-tumor vaccines.

The use of αGal epitopes in inducing a tumor specific response in a prophylactic vaccination-type of protocol has been proposed by others in the field and has been shown to generate protection against a later challenge by the same tumor cells. There is no guarantee, however that the specific TAA's upon which the preventive immune response was generated will be effective against subsequently developed tumor cells. The particular epitope of a TAA for which a prophylactic immune response is generated through preventative vaccination could be specific to that tumor only, that type of cancer only, that patient only or that tissue only etc. The identification of a universal TAA expressed by all cancers has remained elusive and that has prevented the widespread use of prophylactic vaccination strategies for cancer prevention.

Instead of a general prophylactic approach, immune treatment of an individual with recurring, or a diagnosed tumor would provide a more directly targeted method, however there is no consistent expectation that a vaccine methodology will be efficacious as a treatment for already present tumor cells. Several reports have shown effectiveness in prophylactic models, however with the same treatments showing lower or no effectiveness in therapeutic approaches. For example, preventive vaccination with recombinant Vaccinia virus encoding mouse TRP-1 was successful in protecting against subsequent subcutaneous challenge with live tumor B16 cells. This treatment was only partially effective in the prevention of lung melanoma metastasis and was not effective in the treatment of pre-established subcutaneous melanoma, [Overwijk et al, Proc. Natl, Acad. Sci. USA (1999) 96: 2982-2987].

In a similar study, using synthetic oligodeoxynucleotide (ODN) adjuvant containing unmethylated cytosine-guanine motifs (CpG-ODN) and CTLA-4 blockade, the effectiveness of peptide vaccines was evaluated in prophylactic, therapeutic and combination of both treatments. The conclusion of the study was that neither treatment in the preventive or prophylactic mode was effective for B16 melanoma. The authors demonstrated that effective treatment and prolonged survival of mice was observed when mice were vaccinated, challenged with B16 and subsequently they received an additional therapeutic dose of the vaccine. In this study however, vaccination was only partially effective for the treatment of pre-established disease since all mice succumb of melanoma in both the prophylactic, and therapeutic approach [Davila, Kennedy and Celis, Cancer Research (2003), 63: 3281-3288].

Many other studies have focused only on the preventive treatment of subcutaneous melanoma but only few of these have demonstrated a significant and effective therapeutic effect on tumor growth rate but though a reduction in tumor growth rate was not reflected in animal survival [Wang et al, Cancer Research (2003) 63: 2553-2560; Current Protocols of Immunology, Chapter 20, "B16 as a Model for Human Melanoma"].

To further complicate the issue, the presence of tumor specific lymphocytes has been shown to be insufficient to induce tumor destruction. In fact, it has been demonstrated recently that the presence of large amounts of tumor-specific T cells was not sufficient to prolong the survival of tumor-bearing mice [Overwijk et al, Journal of Experimental Medicine, (2003) 198: 569-580]. The authors demonstrated that T cell stimulation through antigen-specific vaccination with an altered peptide ligand, rather than the native self-peptide, and co-administration of a T cell growth and activation factor were three elements strictly necessary to induce tumor regression.

Most tumor cells have unique expression profiles of TAA, but in many cases these TAA are unknown or very difficult to determine or isolate for individual tumors. Moreover, for most tumors that escape immune surveillance the immune system does not recognize these TAA as foreign antigens because either they are not presented in the context of a cellular "danger" signal or because the immune system has been tolerized to those antigens and recognizes them as "self" antigens. The use of whole cell vaccines alleviates the first difficulty, as it provides a whole repertoire of TAA without the need to isolate or characterize those antigens. The use of allogeneic whole cell vaccines provides TAA which might present allelic differences among individuals and therefore might break the tolerance of the immune system to those TAA. Whole cancer vaccines have been also genetically modified to express molecules that enhance the immune response such as GM-CSF [Dranoff et al Proc. Natl. Acad. Sci. USA (1993) 90: 3539]. Genetically modified or unmodified whole cell allogeneic cancer vaccines are showing anti-tumor activity and survival benefits in clinical trials, thereby validating the hypothesis that immune rejection of laboratory produced human cancer cell lines can induce destruction of patient's malignancies. These vaccines function by direct stimulation of cellular immune effectors by direct presentation of TAA in the context of the tumor vaccine Class I MHC which leads to direct activation of cytotoxic T lymphocytes and natural killer cells [van Elsas et al. J. Exp. Medicine (1999) 190: 355-366]. Stimulation of antitumor responses using the previously mentioned approaches has been frequently associated with the triggering of autoimmune disease against the normal tissue of the same cellular type as the tumor tissue. Moreover, these vaccines do not exploit the mechanisms of the humoral branch of the immune system to recognize TAA and to enhance antigen presentation and complement mediated destruction of tumor cells. There are several reasons why a strong humoral immune response should produce a more effective anti-tumor response: I) antibodies that opsonize vaccine cells by binding to specific antigens on the cell surface would promote their phagocytosis by macrophages by binding of the Fc portion of the antibodies to the Fc receptors present on antigen presenting cells. II) Fc receptor targeting accomplishes several important functions for effective vaccine performance including: promoting the efficient uptake of antigen for both MHC Class I and II antigenic presentation; promoting APC activation and promoting the maturation of dendritic cells. III) The uptake of opsonized cells by antigen presenting cells via Fc receptor mediated endocytosis may be critical to generating an effective anti-tumor CTL response since it promotes the activation of MHC class I restricted responses by $CD8^+$ T-cells through a cross-presentation pathway. IV) Vaccines that cannot stimulate a humoral immune response are limited in their ability to induce cellular immunity by HLA restriction. CTLs are HLA restricted and will only destroy the vaccine cells that present tumor antigens on self-class I MHC molecules. NK cells will destroy the tumor vaccine cells if the MHC interaction is poor producing a poor immune response. V) The signals that activate APCs come either directly or indirectly from the naturally acquired immune response. The APCs that ingest tumor vaccine cells must be activated before they can effectively present antigen. Moreover, presenting antigens to immature APCs, without the required activation signals, can suppress the immune response. Furthermore, activated APCs can activate CTLs which cannot kill without activation, even if they recognize their cognate antigen on the HLA matched tumor cells.

From the above discussion it is clear that innovative tumor vaccines are needed in the tumor vaccine field, where the specific needs are: I) to develop tumor vaccines which can cause regression of pre-existing and disseminated tumors or at least that can slow down tumor growth rates in therapeutic settings without the need of preventive vaccination regimes, II) to develop vaccines that stimulate both the cellular and humoral branches of the immune system, and III) to develop vaccines that do not have secondary undesired effects such as the triggering of autoimmune disease.

Applicants' invention provides therapeutic tumor vaccine formulations that satisfy those requirements. The invention comprises the use of gene transfer technique to engineer tumor cells to synthesize $\alpha(1,3)$-Galactosyl epitopes in vitro. The use of the cell's own machinery and the use of a mixture of a number of allogeneic or syngeneic tumor cells that have been so engineered provide for epitopes to be generated on multiple cell surface glycoproteins and glycolipids to provide multiple opportunities for antibodies to be generated to TAAs on individual or separate cells. The cells used in these vaccines are estimated to contain between one and two million $\alpha$Gal epitopes. This large number of binding sites for naturally pre-existing anti-$\alpha$Gal Ab results in a high density of opsonization followed by complement destruction which sets off a variety of processes that activate both the humoral and cellular branches of the immune system. The presence of such a high density of $\alpha$Gal residues on the surface of allogeneic tumor cells induces a hyperimmune response analogous to xenograft hyperacute rejection at the site of the modified tumor cell injection. Furthermore, these cancer vaccines are polyvalent meaning that they present multiple tumor antigen targets to the immune system. This will result in a more efficient treatment in that several TAAs will be presented and in a more widely effective treatment as with the increased number of TAAs presented it is more likely that there will be overlap in epitopes from different individual tumors. Opsonized cells are readily ingested by phagocytes providing a mechanism whereby most of the tumor antigens can be simultaneously presented to the adaptive immune system. Within these cells, proteins from the cancer vaccine cells will be digested and given class II MHC presentation thereby exposing the mutant proteins epitopes in the cancer cell to T-cell surveillance. In addition, the uptake of opsonized cells by antigen presenting cells (APCs) via Fc receptor mediated endocytosis may facilitate the activation of MHC class I restricted responses by CD8$^+$ cells through a cross presentation pathway. The immune system cascade set in motion by this process provides the stimulus to induce a specific T-cell response to destroy native tumor cells from an established human malignancy. Furthermore, the inflammatory environment induced by the primary immune response results in an amplification effect mediated by cytokines, histamines and other up-regulated molecules that boost the T-cell response. T-cells activated in this manner are directly capable of killing cancer cells. An important remark is that the addition of αGal epitopes to glycoproteins and glycolipids present in the tumor vaccine will not restrict the development of an immune response only to those antigens that become glycosylated but to any antigen present within the tumor cell whether it is affected by glycosylation or not.

The effectiveness of this kind of whole cell vaccine at inducing therapeutic tumor immunity has been verified in animal models using knockout (KO) mice. KO mice were generated lacking a functional αGT gene to provide a small animal model to study the in-vivo immune response against αGal epitopes on tumor cell lines. These mice can be immunized with rabbit red blood cells (rRBC) to stimulate a high titer of anti-αGal Ab as found in human serum. Using these mice, applicants have demonstrated that the immune system rejects αGal positive tumor cells and that this rejection leads to the development of T-cell immunity extended to αGal negative tumor cells. This animal model was also used to simulate a clinical application where αGal negative tumor cells were given to the animal prior to treatment with the vaccine to simulate a pre-established human malignancy. By these type of experiments applicants have shown that cell-mediated immunity induced in mice immune-treated with cells engineered according to the invention were able to effectively treat subcutaneous and pulmonary pre-established local and disseminated tumors resulting not only in reduce tumor growth rates but more importantly in long term survival of treated mice. Adoptive cell transfer experiments showed conclusively the cell-dependent component in the rejection of pre-established tumors. The typical autoimmune depigmentation associated to whole cell tumor vaccination described using other approaches was never observed in mice subjected to this treatment highlighting the importance that different immune stimulation methods may have on the final outcome of the immune response.

Thus applicants' invention relates to methods and compositions for causing the selective targeting and killing of pre-established tumor cells. Through ex vivo gene therapy protocols tumor cells are engineered to express a αGal epitopes. The cells are then irradiated or otherwise killed and administered to a patient. The binding of αGal epitope by naturally pre-existing anti-αGal antibodies causes opsonization of the tumor cells and enhances tumor specific antigen presentation. An important feature of the invention contemplates the use of whole cells, and a mixture of a plurality of transduced cells in the pharmaceutical compositions of the invention. Since αGal modifications affect multiple glycoproteins on the cell surface, the animal's immune system will have an increased opportunity to detect, process and generate antibodies to tumor specific antigens.

According to the invention a pharmaceutical composition is generated by introducing to tumor cells a polynucleotide sequence, which encodes upon expression an αGT enzyme. The sequence is introduced through any nucleotide transfer vehicle, which can comprise a viral or non-viral vector. These gene transfer vehicles transform the tumor cells, and cause expression of foreign genetic material inserted therein. The resulting gene product catalyzes the synthesis of an αGal epitope, on cell surface glycoproteins present on said cells. The invention contemplates the use of whole tumor cells with multiple cell surface glycoproteins to maximize the binding of αGal epitopes by pre-existing anti-αGal antibodies thus enhancing binding of this complexes to the Fc receptors present on antigen presenting cells and thus triggering antigen presentation of a plurality of tumor associated antigens present in said vaccine tumor cell.

The invention also comprises a pharmaceutical composition and a method for making the same, which includes a therapeutically effective amount of a mixture of attenuated tumor cells said mixture comprising a plurality of cell surface glycoproteins which include αGal epitopes and a carrier. In a preferred embodiment the cells are whole cells. Methods for making the compositions include obtaining a collection of live tumor cells, transforming said cells with a nucleotide sequence that encodes upon expression an αGT so that an αGal epitope is presented on cell surface glycoproteins of said cells. The cells are then killed, preferably by irradiation and combined with a pharmaceutical carrier for administration.

Yet another embodiment of the invention comprises the transformation of tumor cells with a polynucleotide which will create an αGal epitope on the tumor cells. One embodiment of the invention comprises transformation of tumor cells with a nucleotide sequence which encodes upon expression, the enzyme α-(1,3)-galactosyl transferase (αGT). The αGT cDNA has been cloned from bovine and murine cDNA libraries. Larson, R. D. et al. (1989) "Isolation of a cDNA Encoding Murine UDP galactose; .βD-galactosyl-1,4-N Acetol-D-Glucosamine α1-3 Galactosyl Transferase: Expression Cloning by Gene Transfer", PNAS, USA 86:8227; and Joziasse, D. H. et al., (1989) "Bovine α1-3 Galactosyl Transferase: Isolation and Characterization of a cDNA Clone, Identification of Homologous Sequences in Human Genomic DNA", J. Biol Chem 264:14290. Any other nucleotide sequence which similarly will result in the tumor cells expressing an αGal epitope on the cell surface may be used according to the invention, for example other enzymes that catalyze this reaction or perhaps event the engineering of the cells to have additional glycoproteins present on the cell surface hence the artificial creation of a TAA which can be presented to the immune system.

The tumor cells used for the pharmaceutical composition of the invention may be autologous, or in a preferred embodiment may be allogeneic or syngeneic. The transformed cells and the tumor cells to be treated must have at least one epitope in common, but will preferable have many. To the extent that universal, or overlapping epitopes or TAA exist between different cancers, the pharmaceutical compositions may be quite widely applicable.

The invention also need not be limited to a cancer cell and can include any cell surface glycoprotein-containing cell, or cell component that has a site for an αGal epitope. This may include certain viruses, neoplastic cells, and the like.

The nucleic acid sequence that encodes the αGal epitope generating protein is contained in an appropriate expression vehicle, which transduces the tumor cells. Such expression vehicles include, but are not limited to, eukaryotic vectors, prokaryotic vectors (such as, for example, bacterial vectors), and viral vectors.

In one embodiment, the expression vector is a viral vector. Viral vectors which may be employed include, but are not limited to, retroviral vectors, adenovirus vectors, Herpes virus vectors, and adeno-associated virus vectors, or DNA conjugates.

In a preferred embodiment, a viral vector packaging cell line is transduced with a viral vector containing the nucleic acid sequence encoding the agent which induces the destruction of the tumor cells by antibody binding and complement activation. The viral particles produced by the packaging cell line are harvested and used to transduce the tumor cells which will be administered as the anti-tumor vaccine.

Traditionally, the viral vector is a retroviral or adenoviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., J. Virol. 61:1639-1649 (1987), based on the N2 vector (Armentano, et al., J. Virol., 61:1647-1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point.

Figure 1:
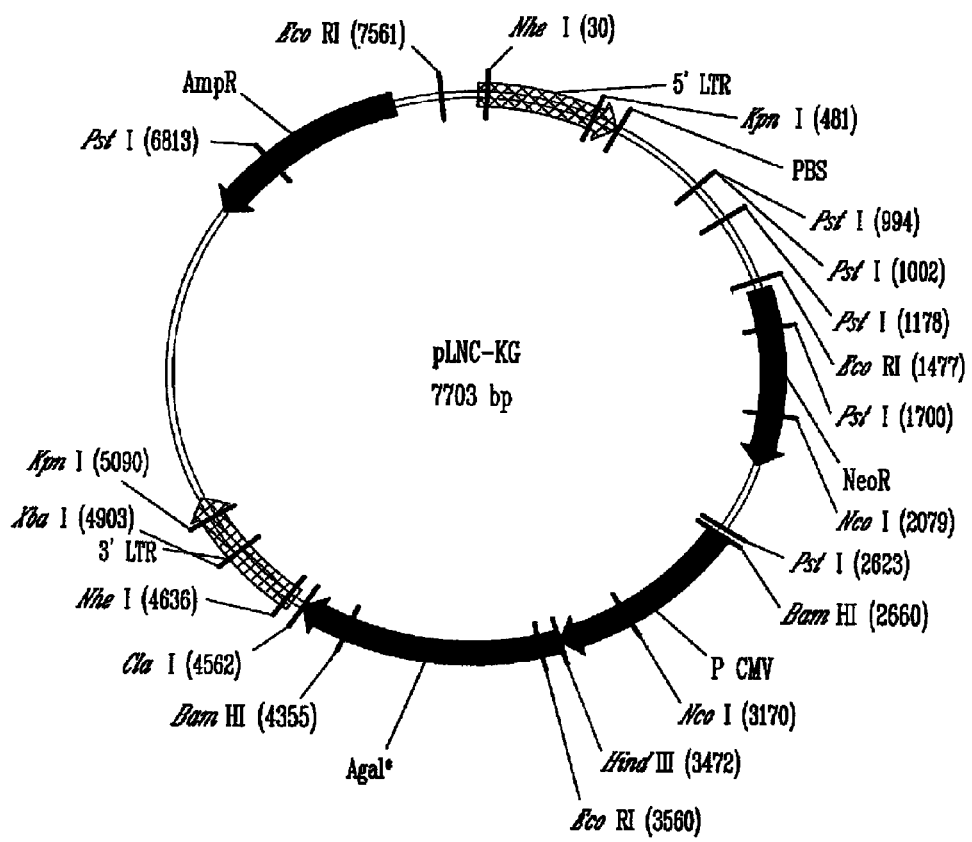
FIG. 1 is a depiction of the pLNC-KG plasmid which may be used according to the invention.

In Moloney murine leukemia virus (MoMuLV), 5' to the authentic gag start, an open reading frame exists which permits expression of another glycosylated protein (pPr80.sup.gag). Moloney murine sarcoma virus (MoMuSV) has alterations in this 5' region, including a frameshift and loss of glycosylation sites, which obviate potential expression of the amino terminus of pPr80.sup.gag. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., Biotechniques, 7:980-990, 1989). One example of a vector which may be used according to the invention is shown in FIG. 1, which the sequence shown in FIG. 2, SEQ ID NO:1.

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters.

In another embodiment the invention comprises an inducible promoter. One such promoter is the tetracycline-controlled transactivator (tTA)-responsive promoter (tet system), a prokaryotic inducible promoter system which has been adapted for use in mammalian cells. The tet system was organized within a retroviral vector so that high levels of constitutively-produced tTA mRNA function not only for production of tTA protein but also the decreased basal expression of the response unit by antisense inhibition. See, Paulus, W. et al., "Self-Contained, Tetracycline-Regulated Retroviral Vector System for Gene Delivery to Mammalian Cells", J of Virology, January. 1996, Vol. 70, No. 1, pp. 62-67. The selection of a suitable promoter will be apparent to those skilled in the art from the teachings contained herein.

The vector then is employed to transduce a packaging cell line to form a producer cell line. Examples of packaging cells which may be transfected include, but are not limited to the PE501, PA317, .psi.2, .psi.-AM, PA12, T19-14X, VT-19-17-H2, .psi.CRE, .psi.CRIP, GP+E-86, GP+envAM12, DAN and AMIZ cell lines. The vector containing the nucleic acid sequence encoding the agent which is capable of providing for the destruction of the tumor cells upon expression of the nucleic acid sequence encoding the agent, and activation of the complement cascade may transduce the packaging cells through any means known in the art. Such means include, but are not limited to, electroporation, the use of liposomes, and $CaPO_4$ precipitation.

In a preferred embodiment the invention comprises a viral vector which commonly infects humans and packaging cell line which is human based. For example vectors derived from viruses which commonly infect humans such as Herpes Virus, Epstein Barr Virus, may be used.

Tumors which may be treated in accordance with the present invention include malignant and non-malignant tumors. Malignant (including primary and metastatic) tumors which may be treated include, but are not limited to, those occurring in the adrenal glands; bladder; bone; breast; cervix; endocrine glands (including thyroid glands, the pituitary gland, and the pancreas); colon; rectum; heart; hematopoietic tissue; kidney; liver; lung; muscle; nervous system; brain; eye; oral cavity; pharynx; larynx; ovaries; penis; prostate; skin (including melanoma); testicles; thymus; and uterus. Examples of such tumors include apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), plasmacytoma, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's experimental, Kaposi's, and mast-cell), neoplasms and for other such cells.

Pharmaceutical Preparations

According to the invention attenuated αGal expressing tumor cells are used as either prophylactic or therapeutic vaccines to treat tumors. Thus the invention also includes pharmaceutical preparations for humans and animals involving these transgenic tumor cells (expressed as HA1 HA2 etc., see Table 1). Those skilled in the medical arts will readily appreciate that the doses and schedules of pharmaceutical composition will vary depending on the age, health, sex, size and weight of the human and animal. These parameters can be determined for each system by well-established procedures and analysis e.g., in phase I, II and III clinical trials and by review of the examples provided herein.

For administration, the attenuated tumor cells can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

Suitable formulations for parenteral, subcutaneous, intradermal, intramuscular, oral or intraperitoneal administration, include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers. Also, tumor vaccine cells can be mixed with immune adjuvants well known in the art such as Freund's complete adjuvant, inorganic salts such as zinc chloride, calcium phosphate, aluminum hydroxide, aluminum phosphate, saponins, polymers, lipids or lipid fractions (Lipid A, monophosphoryl lipid A), modified oligonucleotides, etc.

In addition to administration with conventional carriers, active ingredients may be administered by a variety of specialized delivery drug techniques which are known to those of skill in the art. The following examples are given for illustrative purposes only and are in no way intended to limit the invention.

The invention will now be described with respect to the following examples; however, the scope of the present invention is not intended to be limited thereby. All citations to patents and journal articles are hereby expressly incorporated by reference.

Example 1

Production of Retroviral Vector Expressing αGT, pLNCKG

A 1,077 bp fragment of murine αGT gene was PCR amplified by a forward primer, 5'-ACAAAAGCTTGACATGGAT-GTCAAGGGAAAAGTAAT-3', which contains a Kozak sequence to enhance the translation of αGT, and a reverse primer, 5'-AATTATCGATTCAGACATTATTTCTAAC-3', and then cloned into the ClaI and HindIII sites of pLNCX to produce pLNCKG retroviral vector (FIG. 1). This vector was transfected into the packaging cell line 293.AMIZ [Young and Link "Chimeric retroviral helper virus and picornavirus IRES sequence to eliminate DNA methylation for improved retroviral packaging cells" J. Virol. (2000) 74: 5242-5249] to generate the vector producer cell line 293.AMIZ/LNCKG. Transfected cells were selected in presence of G418 and Zeocin™ for two weeks. Mixed population of selected cells was subcloned by limiting dilutions. Single cell-derived VPC were screened for their ability to effectively transduce human epithelial cancer cell lines established from different tissues. The clone which supernatant consistently yielded highest transduction efficiency and αGT expression on a panel of human epithelial cancer cell lines was identified and designated 293Z.CKG VPC. A master cell bank, working cell bank and production lot was generated for 293Z.CKG VPC was originated from one vial of the seed bank, expanded in flasks at 37° C.±1° C. in 5%±1% CO2. The culture medium was RPMI-1640 supplemented with 10% fetal bovine serum (FBS) and 2 mm L-glutamine. When the 293Z.CKG VPC reached sufficient density, the culture fluids (supernatant) are harvested, filtered, and pooled into a sterile container. The pool is thoroughly mixed and then aseptically filled into labeled, sterile plastic bottles. (Labels contain the product name, lot number and date of filling.) The fill bottles are frozen and stored at or below −60° C. Aliquots are submitted for safety testing. Retrovirus-containing supernatants from 293Z.CKG VPC were used to transduce different human cancer cell lines (mentioned in examples below) to establish the αGal$^{(+)}$ whole cell vaccines.

Example 2

Transduction of B16.BL6 Melanoma Cells with LNCKG Retroviral Vector

To generate αGal$^{(+)}$ B16 cells, $2\times10^6$ cells were transduced with 2 mL of supernatant containing the LNCKG retrovirus with an infectious titer of $2\times10^6$ tu/mL. Cells were selected for resistance to Neomycin by a two-week selection in medium supplemented with G418 1 mg/mL. After this period of selection, cells were stained for expression of the αGal epitope with a chicken anti-αGal polyclonal antibody and sorted by fluorescence activated cell sorting.

Example 3

Figure 3:
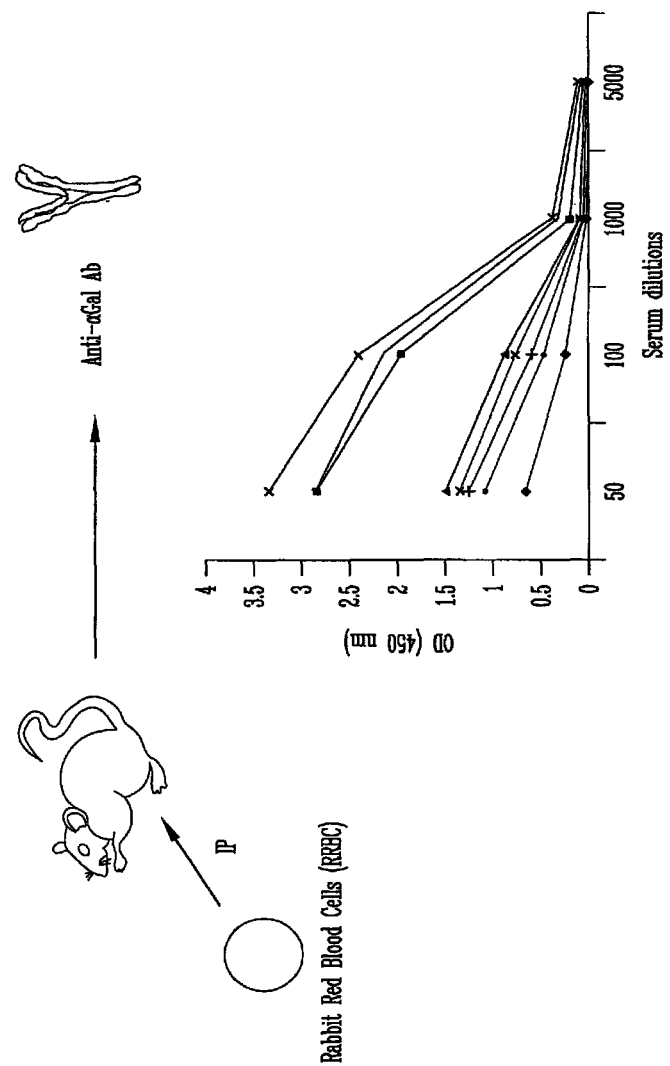
FIG. 3 is a schematic of induction of Anti-αGal antibodies in α(1,3)-galactosyl transferase knockout (αGT KO) mice by immunization with rabbit red blood cells. To induce anti-αGal antibodies (Ab), mice were injected intraperitoneally with $10^8$ rabbit red blood cells (RRBC) twice, two weeks apart. One week after the last immunization, blood samples were obtained and anti-αGal antibody titers were determined by ELISA. All mice used in this study developed high titer of anti-αGal Ab.

Induction of Anti-αGal Antibodies in α(1,3)-galactosyltransferase Knockout (αGT KO) Mice by Immunization with Rabbit Red Blood Cells Females and males 8 to 14 weeks old α-(1,3)galactosyltransferase (αGT) knockout (KO) mice were used in this study. Mice were initially of mixed haplotype (H-2 b/d) and by breeding and selection the current colony of αGT KO mice was obtained consisting in F4 inbreeding generation of H-2 b/b haplotype. These animals produce low titers of natural antibodies against αGal epitopes. To increase the titer of anti-αGal Ab mice were immunized intraperitoneally (i.p.) with $1\times10^8$ Rabbit Red Blood Cells twice, two weeks apart. The titers of anti-αGal Ab were checked one week after the last RRBC injection to corroborate that all mice in the study have high titers of anti-αGal Ab. All mice used in this study have high anti-αGal Ab titers greater than 1:500 dilution, measured by ELISA. A representative experiment is shown in FIG. 3.

Example 4

Figure 4:
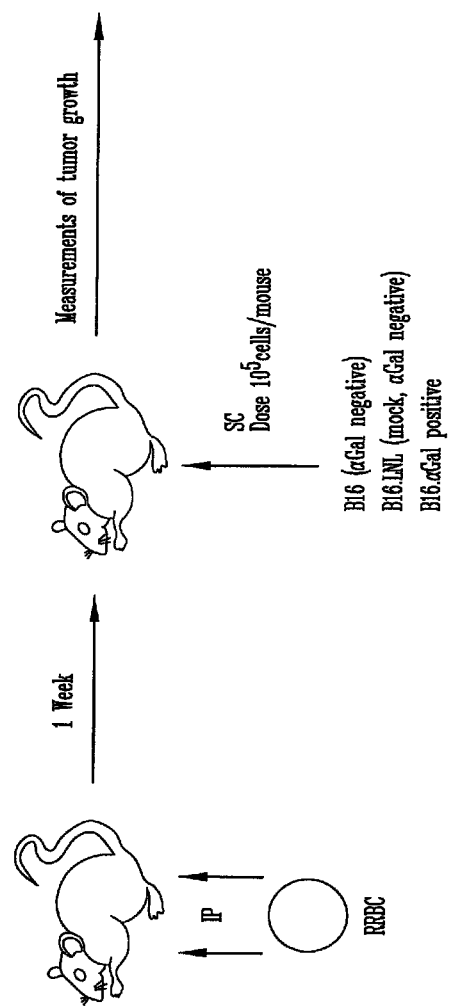
FIG. 4 is a schematic showing survival test after subcutaneous injection of a lethal dose of non-irradiated $\alpha Gal^{(+)}$ or $\alpha Gal^{(-)}$ B16 melanoma cells. Females and males 8 to 14 weeks old H-2 b/b haplotype αGT KO mice were used in this study. All mice were immunized with RRBC as showed in FIG. 3. One week after the last immunization, mice received a lethal subcutaneous (subcutaneous) challenge of $1 \times 10^5$ of either of these three cell lines: a) wild type B16.BL6 melanoma cell line ($\alpha Gal^{(-)}$), b) B 16 cell retrovirally transduced with a vector expressing Neo-R gene (B16.LNL, mock control $\alpha Gal^{(-)}$) or c) B16 cells retrovirally transduced with a vector expressing both, NeoR gene and αGT (B16 $\alpha Gal^{(+)}$, pLNCKG). After challenge, tumors were measured in a blinded manner twice a week.

Survival Test after Subcutaneous Injection of a Lethal Dose of Non-Irradiated αGal$^{(+)}$ or αGal$^{(-)}$ B16 Melanoma Cells The goal of this experiment was to determine if the expression of αGal epitopes in cancer cells would lead to their in vivo hyperacute rejection in hosts with pre-existing anti-αGal Ab. Thus RRBC-injected αGT KO mice were challenged with non-irradiated $10^5$ B16 melanoma cells expressing or not the αGal epitopes and tumor development was measured (FIG. 4).

Figure 5A:
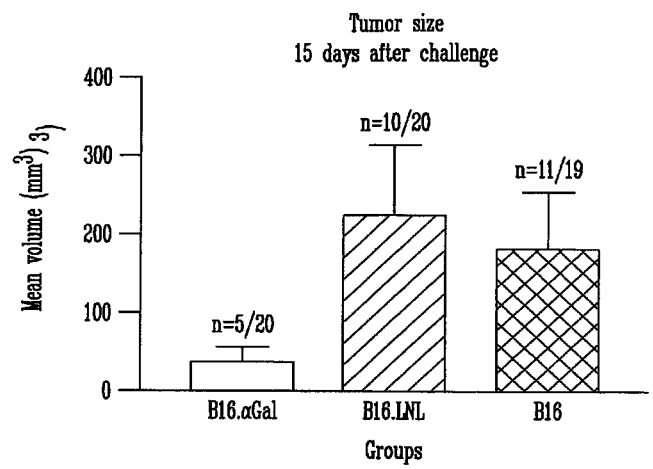
FIGS. 5a and 5b are graphs showing tumor size after subcutaneous injection (5a—15 days after challenge, 5b—30 days after challenge) of lethal doses of non-irradiated $\alpha Gal^{(+)}$ or $\alpha Gal^{(-)}$ B16 melanoma cells in αGT knockout mice. Palpable subcutaneous tumors were measured with a caliper in three perpendicular axes the volume calculated and expressed in $mm^3$. The figure depicts tumor sizes at 15 and 30 days after subcutaneous injection with the respective B16 cell line described in FIG. 4. The bars represent the mean and errors bars the SEM.
Figure 5B:
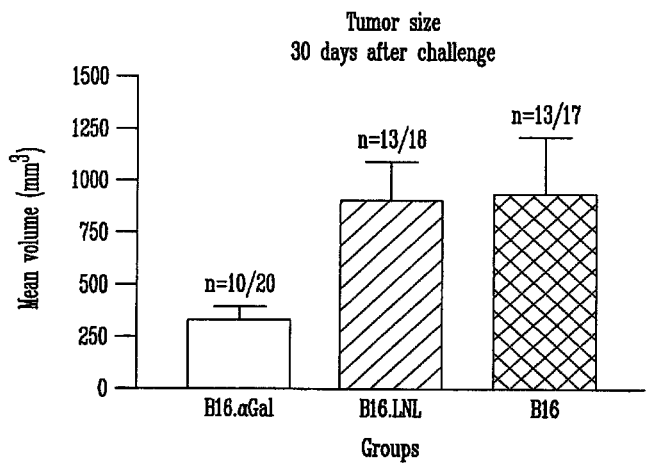

FIG. 5 shows tumor size 15 days after the challenge. As expected, 11 of 19 mice that received native αGal$^{(-)}$ B16 developed measurable tumors two weeks after the challenge. Similarly 10 of 20 mice receiving the B16.LNL αGal$^{(-)}$ B16 cells developed tumors (57% and 50%, respectively. Chi square p>0.05, not significant). However, when mice received the αGal$^{(+)}$ B16 cells, significant fewer animals developed tumors. Only 5 out of 20 animals (25%) developed palpable tumors (Chi square, p=0.03 significantly different from control). In addition, tumors were considerable larger in animals challenged with the control and mock transduced cells compared with tumor developed in mice receiving the αGal-expressing cells. Average sizes of 200 mm$^3$ tumors were observed in both controls groups with differences between groups not being statistically significant (F test p=0.38). However, a significant difference was observed in the tumor size in the group receiving the B16.αGal$^{(+)}$ cells. The mean size tumor of the test group was 36 mm$^3$, which represents about 80% reduction in the tumor size compared with control animals (F test p=0.002).

This result demonstrates that fewer animals developed smaller tumors when challenged with αGal-expressing B16 cells indicating that anti-αGal pre-sensitized mice are able to mediate more effective in vivo clearance of αGal expressing cells compared with the native or mock transduced αGal negative B16 controls.

Comparable results were observed when tumors were measured 30 days after the challenge. Thirteen mice had tumors out of 17 mice in the group that received B16 wild type (76%). Similarly 13 out of 18 mice developed large tumors in the group receiving cells transduced with mock vector (72%). However, only 50% of mice had measurable tumors in the group receiving the αGal-expressing cells. More importantly, a total of four animals, two in each of the control groups, had to be euthanized because of the development of large tumors. None of the animals that received the αGal expressing cells died by thirty days after tumor implantation, indicating an increase in the survival of animal challenged with αGal expressing cells.

Figure 6:
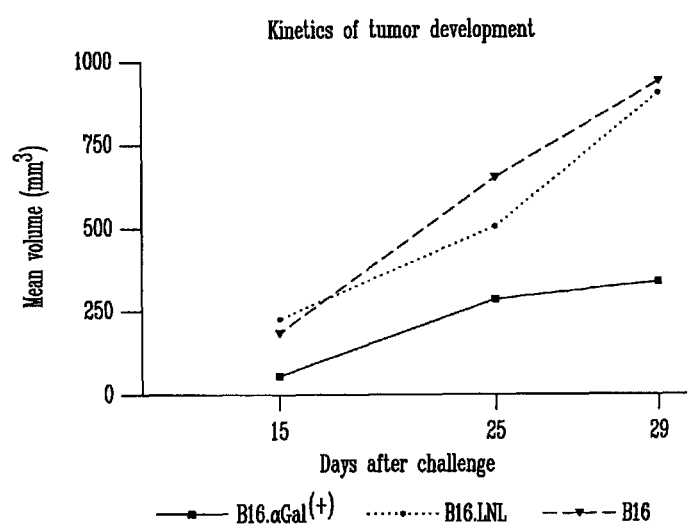
FIG. 6 is a graph showing tumor growth kinetics after subcutaneous injection of a lethal doses of non-irradiated $\alpha Gal^{(+)}$ or $\alpha Gal^{(-)}$ B16 melanoma cells in αGT KO mice. Tumor sizes were measured as in FIG. 5 at 15, 23 and 29 days after challenge with: wild type B16 ($\alpha Gal^{(-)}$), B16.LNL (control $\alpha Gal^{(-)}$) and $\alpha Gal^{(+)}$ B16.

FIG. 6 shows the kinetics of tumor development after challenge with control, mock and αGal-expressing B16 cells. Tumors in both control αGal$^{(-)}$ groups grew extremely fast almost doubling the volume every 7 days. On the contrary, tumors from mice challenged with αGal$^{(+)}$ B16 cells grew significantly slower at early time points (p=0.03). This suggests that immune mechanism(s) may restrain the growth of the tumor and help prolong the survival of tumor-bearing mice.

Long-Term Survival of Mice after Lethal Challenge with αGal$^{(+)}$ B16 Cells

Figure 7A:
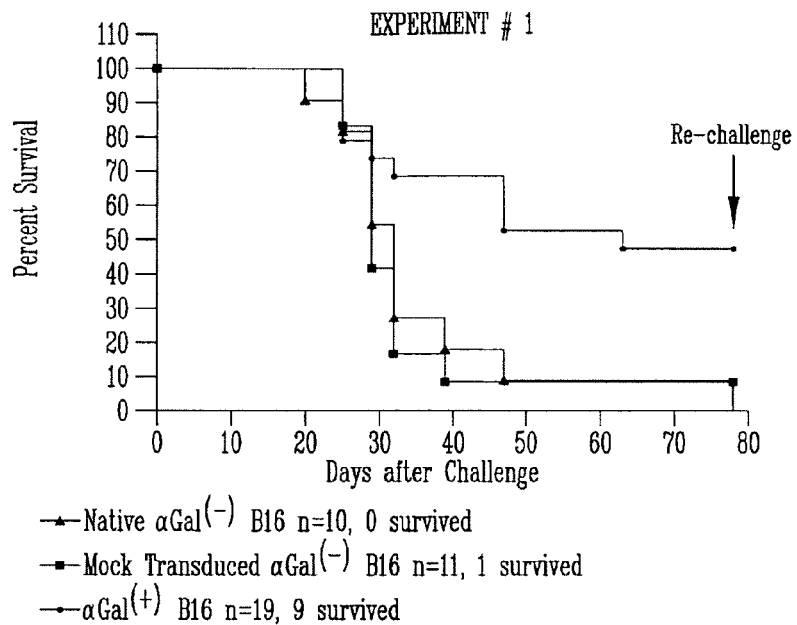
FIGS. 7a and 7b are graphs showing survival analysis of αGT KO mice lethally injected with non-irradiated $\alpha Gal^{(+)}$ or $\alpha Gal^{(-)}$ B16 melanoma cells. Mice treated as described in FIG. 4 were studied for 90 days. Kaplan-Meier survival analysis and long-rank survival curves comparisons were performed using statistics software.
Figure 7B:
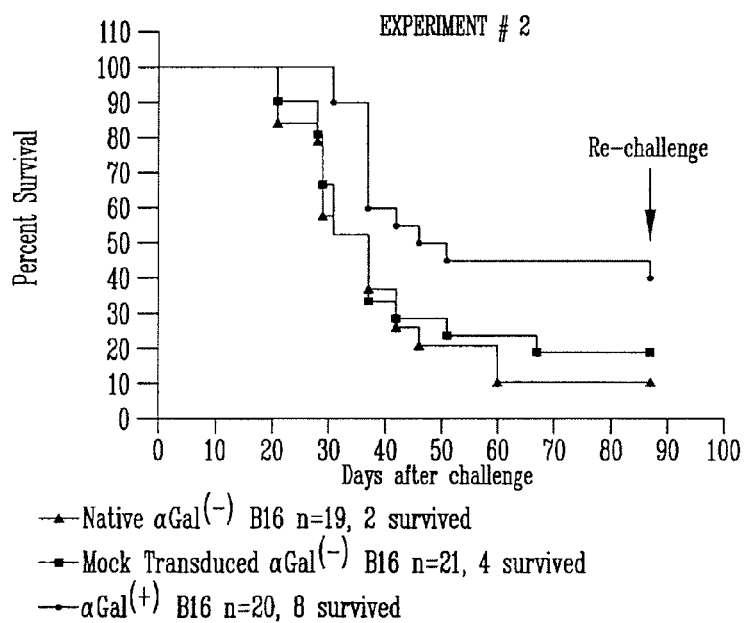

Mice from groups that received control αGal$^{(-)}$, mock transduced αGal$^{(-)}$ B16 and αGal$^{(+)}$ B16 were observed weekly during 90 days (FIG. 7). As shown in the figure, none out of 10 animals receiving native B16 survived the challenge and only one mice out of 11 receiving mock-transduced αGal$^{(-)}$ B16 cells survived the subcutaneous injection. Both control groups showed very similar survival curves, indicating that the NeoR gene product is not inducing a significant change in the rejection and/or immunogenicity of B16 (Logrank Test p=0.5, differences not statistically significant). On the contrary, 47% of the animals receiving αGal-expressing non-irradiated B16 cells survived the lethal challenge. Nine out of 19 mice remained tumor free for 80 days after the subcutaneous injection. Using Kaplan-Meier survival analysis a significant increase in the survival proportion was observed in the group subcutaneous injected with αGal$^{(+)}$ B16 cells compared to control groups (Logrank Test p<0.02).

In both control groups injected with αGal$^{(-)}$ B16, near 60% of the animals died in the first 30 days after challenge. On the contrary the experimental group injected with αGal$^{(+)}$ B16 only five animals (26%) had to be euthanized in the first month after challenge.

In a second independent experiment similar results were obtained. Only 2 out of 19 mice injected subcutaneous with native αGal$^{(-)}$ B16 survived. Comparably, only 4 out of 21 mice survived the lethal subcutaneous challenge with mock transduced αGal$^{(-)}$ B16 cells. On the contrary, 8 out of 20 mice injected subcutaneous with αGal$^{(+)}$ B16 survived and remained tumor free for more than 80 days.

Altogether this result demonstrates that the expression of αGT gene and the change in the glycosilation pattern of B16 induce in vivo destruction of living cancer cells that helped reduce tumor growth prolonging the survival of tumor-bearing mice. More importantly, since about 40% of challenged mice remained tumor free, the injection of αGal expressing cells may lead to the induction of a strong immune response able to control the growth of highly lethal αGal$^{(-)}$ melanoma cells.

Survival after Lethal Challenge with Non-Irradiated αGal$^{(+)}$ B16 Cells Lead to Induction of Memory Protective Immunity Against Wild Type αGal$^{(-)}$ B16

Figure 8:
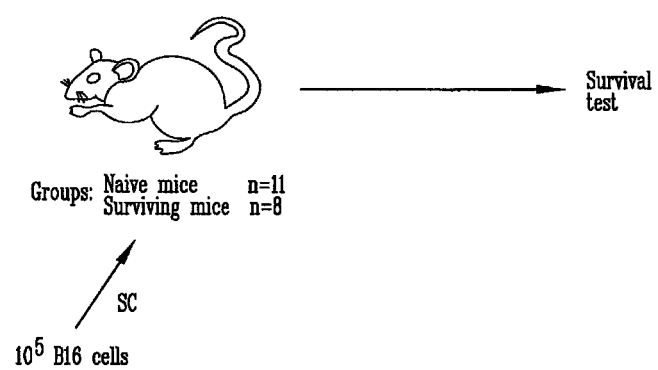
FIG. 8 is a schematic depicting the experimental design for survival test after the lethal subcutaneous injection of non-irradiated $\alpha Gal^{(-)}$ B16 melanoma cells in mice that survived a lethal injection of non-irradiated $\alpha Gal^{(+)}$ B16 melanoma cells.
Figure 9:
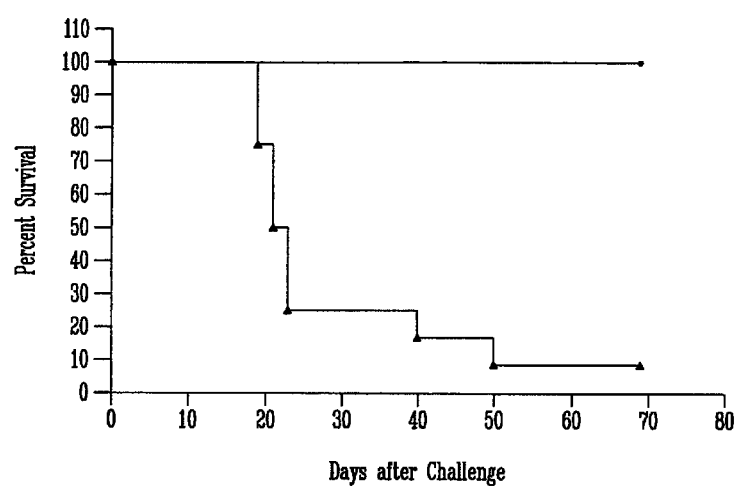
FIG. 9 is a graph showing survival analysis of knockout mice. Mice that survived the first challenge with $\alpha Gal^{(+)}$ B16 cells from FIG. 7, were subsequently challenged with a second subcutaneous dose of native $\alpha Gal^{(-)}$ B16 (FIG. 8). Kaplan-Meier analysis was performed for a period of 60 days after the injection of $\alpha Gal^{(-)}$ B16. Naïve mice receiving $\alpha Gal^{(-)}$ B16 subcutaneous were used as controls.

We hypothesized that surviving animals from the subcutaneous injection of non-irradiated αGal$^{(+)}$ B16 cells, developed cellular immunity extended to the native αGal$^{(-)}$ B16 tumor. To test this hypothesis all surviving tumor-free mice were re-challenged with wild type B16 (αGal negative). Aged-matched mice were included as controls and were also injected with αGal$^{(-)}$ B16 (FIG. 8). As expected 11 out of 12 control mice challenged with αGal$^{(-)}$ B16 died from subcutaneous melanoma developing large and pigmented tumors (FIG. 9). On the other hand, none of the mice that survived the first encounter with non-irradiated αGal$^{(+)}$ B16 melanoma developed tumors. All 8 mice remained tumor free for 70 days increasing significantly the survival of mice that first rejected αGal$^{(+)}$ B16 cells (logrank test p<0.001). Interestingly, protection against B16 melanoma was not associated with autoimmune depigmentation (vitiligo) as previously described by others [Overwijk et al. "Vaccination with a recombinant vaccinia virus encoding a self antigen induces autoimmune vitiligo and tumor cell destruction in mice: requirement for CD4+ T lymphocytes" Proc. Natl. Acad. Sci. USA (1999) 96: 2982-2987; Overwijk et al. "Tumor regression and autoimmunity after reversal of functionally tolerant state of self-reactive CD8+ T cells" J. Exp. Med. (2003) 198: 569-580; van Elsas et al. "Combination immunotherapy of 916 melanoma using anti-CTLA-4 and GM-CSF-producing vaccines induces rejection of subcutaneous and metastatic tumors accompanied by autoimmune depigmentation" J. Exp. Med. (1999) 190: 355-366].

This result demonstrated that mice that survived the lethal challenge with αGal$^{(+)}$ cells developed strong immunity against the native αGal$^{(-)}$ tumor. This cellular and possibly humoral immune response protected surviving mice from a second lethal challenge with wild tumor indicating that the immune response has been extended to native αGal$^{(-)}$ tumor B16 in all protected mice.

To further demonstrate the hypothesis that T cell mediated immunity was induced in protected mice, melanoma specific T cell cultures were generated and tested against αGal$^{(-)}$ B16 melanoma, and the non-specific cell lines EL-4 and MC38 (FIG. 10).

As shown in FIG. 11, strong CTL able to lyse B16 melanoma specifically were induced in protected mice measured by LDH release in target cells.

Altogether, these results demonstrate that the injection of αGal$^{(+)}$ cells increased the survival in mice. Moreover, mice that rejected αGal$^{(+)}$ B16 cells and survived the initial lethal injection, were able to develop strong immunity extended against the native αGal$^{(-)}$ B16 melanoma tumor. This indicates that memory T cell mediated immunity was induced after rejection of αGal$^{(+)}$ B16 cells able to recognize αGal$^{(-)}$ B16 tumor protecting mice from a lethal tumor dose.

Example 5

Disseminated Melanoma Metastasis Model in the αGT Knockout Mice by Intravenous Injection of a Lethal Dose of Non-Irradiated αGal$^{(+)}$ or αGal$^{(-)}$ B16 Melanoma Cells To further demonstrate that mice with high titer of anti-αGal Ab are able to reject αGal$^{(+)}$ B16 melanoma cells, the lung melanoma metastasis model was used. Mice were intravenously (i.v) injected with $10^5$ non-irradiated αGal$^{(-)}$ or αGal$^{(+)}$ B16 melanoma cells. Three weeks later, the lung melanoma metastases were enumerated (FIG. 12). Mice injected with αGal$^{(-)}$ B16 cells have many lung metastasis. On the contrary mice injected with αGal$^{(+)}$ B16 cells have reduced lung burden (FIG. 13). Moreover two out of 5 mice were tumor free. This result indicates that pre-existing anti-αGal Ab played a major role in the clearance of αGal$^{(+)}$ B16 cells.

Example 6

Prevention of Subcutaneous Tumor Development by Prophylactic Vaccination with αGal$^{(+)}$ Cells The goal of this experiment was to determine whether the prevention of subcutaneous tumors could be accomplished by vaccination with αGal$^{(+)}$ vaccines as previously described [LaTemple et al. "Increased immunogenicity of tumor vaccines complexed with anti-αGal: studies in knockout mice for α1,3galactosyltransferase" Cancer Res. (1999) 59:3417-3423]. Mice were immunized with RRBC as described previously. One week after the last RRBC injection mice received the first dose of irradiated cell vaccine. Mice were injected either with irradiated native αGal$^{(-)}$ B16, αGal$^{(-)}$ B16 transduced with control vector (pLNL, encoding for Neomycin Resistance Gene) or with αGal$^{(+)}$ B16 (transduced with vector encoding the Neomycin Resistance Gene and the αGT gene). Some mice did not receive irradiated cell vaccines. The cell vaccination was repeated two weeks later. Two weeks after the last vaccination mice were injected subcutaneous with $10^5$ non-irradiated αGal$^{(-)}$ B16 cells (FIG. 14). Tumors were measured twice a week for 90 days. As shown in FIG. 15, zero out of 10 mice that did not received B16 cell vaccines survived the challenge and died before 50 days after challenge. Some protection was observed in mice vaccinated with native αGal$^{(-)}$ B16 and with αGal$^{(-)}$ B16/NeoR vaccines. Four 4 out of 14 and 5 out of 12 mice survived the B16 challenge, respectively. There is not statistical difference between mice vaccinated with B16 and B16/NeoR which indicates that under this conditions NeoR gene product does not increase immunogenicity of B16 (p>0.2, Logrank test). On the contrary, significant more protection was observed when mice were vaccinated with αGal$^{(+)}$ B16 cells since 12 out of 20 mice survived the challenge and remained tumor free for more than 90 days (p<0.001, ANOVA, p=0.08 Logrank test). This result demonstrates that vaccination with irradiated αGal$^{(+)}$ cells prevents the development of subcutaneous melanoma tumors in 60% of αGal$^{(+)}$ B16 vaccinated mice and significantly prolonged the survival of mice challenged with αGal$^{(-)}$ B16 melanoma.

We hypothesized that T cells able to recognize the native αGal$^{(-)}$ B16 cells were induced after vaccination with αGal$^{(+)}$ B16 vaccine in mice protected from the injection with live αGal$^{(-)}$ B16. To test this hypothesis, splenocytes from mice vaccinated with αGal$^{(+)}$ vaccines were harvested and cultured for 6 h in presence or absence of stimulation. For maximum stimulation PMA/Ca$^{++}$ Ionophore was used. Cells were cultured with $10^5$ irradiated B16 cells to measure specific recognition or with CA320M, a non-specific αGal$^{(-)}$ cell line with identical H-2 b/b haplotype. After incubation cells were harvested and stained for intracellular TNF-α. Detection was performed by FACS gating in lymphocytes in the Forward Scatter plot (FIG. 16). T cells harvested from αGal$^{(+)}$ B16 vaccinated mice were efficiently activated by PMA/Ca++ Ionophore. The percentage of lymphocytes activated by this polyclonal activator method is considered the maximum activation detected in this experiment. Resting (unstimulated) T cells and T cells stimulated with CA320M were not able to produce TNF-α, indicating that no T cells precursors were induced after B16-αGal$^{(+)}$ vaccination able to recognize antigens in CA320M. On the contrary, vaccination with B16-αGal$^{(+)}$ induced T cell precursor that specifically recognize B16-αGal$^{(-)}$ in vitro. This result suggests that these T cells induced after vaccination with αGal$^{(+)}$ B16 maybe responsible for tumor prevention in about half of αGal$^{(+)}$ B16 treated mice.

Example 7

Treatment of Pre-Established Subcutaneous Melanoma Tumors by αGal$^{(+)}$ Cell Vaccination Since the vaccination with native αGal$^{(-)}$ B16 and αGal$^{(+)}$ mock-transduced B16/NeoR resulted in similar data in the experiments shown above the following experiments were performed with vaccination using irradiated αGal$^{(-)}$ B16/NeoR alone as negative control to increase the power of the statistical analysis.

The goal of the next experiment was to determine whether the treatment of pre-established subcutaneous melanoma tumors could be accomplished by vaccination with αGal$^{(+)}$ B16 vaccines. It is not obvious that the effective preventive treatment will be also effective in the treatment of pre-established tumors. In the particular case of B16 melanoma as tumor model, several strategies have been proved effective in preventive schedules of immunization and have had low or no impact in the treatment of pre-established subcutaneous melanoma tumors. For example, the vaccination with recombinant vaccinia virus encoding mouse mTRP-1 prevents the development of subcutaneous melanoma tumors and has no impact in the treatment of pre-established subcutaneous tumors [Overwijk et al. "Vaccination with a recombinant vaccinia virus encoding a self antigen induces autoimmune vitiligo and tumor cell destruction in mice: requirement for CD4+ T lymphocytes" Proc. Natl. Acad. Sci. USA (1999) 96: 2982-2987]. Similarly, peptide specific immunization leads to the induction of strong T cell immunity but it is rarely effective for the treatment against pre-established tumors (Davila et al. "Generation of antitumor immunity by cytotoxic T lymphocyte epitope peptide vaccination, CpG oligodeoxynucleotide adjuvant and CTLA-4 blockade" Cancer Research (2003) 63:3281-3288]. Moreover, the sole presence of tumor specific T cell is a condition necessary but it is not sufficient to effectively induce tumor eradication.

We hypothesized that αGal$^{(+)}$ vaccines will induce strong cell dependent tumor immunity able to reject pre-established αGal$^{(-)}$ tumors. To test this hypothesis we conducted experiments designed to treat pre-established tumors (FIG. 17).

Mice were injected subcutaneous with non-irradiated $10^5$ B16 cells and randomized. Three days after challenge they were vaccinated subcutaneous with irradiated αGal$^{(-)}$ B16/NeoR or with irradiated αGal$^{(+)}$ B16. Three days later the vaccination with irradiated cell vaccines was repeated. The baseline control mice received subcutaneous injection with non-irradiated B16 and they did not receive irradiated cell vaccine treatment (No vaccine group). FIG. 18 a and b show the kinetics of tumor growth of non-vaccinated mice (n=11), mice vaccinated with αGal$^{(-)}$ B16/NeoR (n=24) and mice receiving αGal$^{(+)}$ B16 vaccine (n=23). The data represents the mean and error bars, the SEM. Statistical analysis indicates a significant difference of the slopes, when comparing control mice with mice receiving αGal$^{(+)}$ B16 cell vaccines (p<0.009), This result indicates that mice vaccinated with irradiated αGal$^{(+)}$ B16 vaccines developed smaller tumors that grew slower.

In Experiment #2, mice received and additional dose of cell vaccine. Mice receiving only the subcutaneous injection with non-irradiated αGal$^{(-)}$ B16 developed large tumors that grew very fast during the first month of observation (n=15). Similarly, mice injected with control αGal$^{(-)}$ B16 vaccine developed large tumors growing very fast (n=29). The statistical comparison of the slopes of these two groups indicated that they were not significantly different (p=0.17). This indicates that the vaccination with αGal$^{(-)}$ B16/NeoR has no impact in the treatment of subcutaneous pre established melanoma tumors. On the contrary mice receiving αGal$^{(+)}$ B16 vaccines, developed smaller tumors that grew slower (n=33). There was a statistically significant difference in the tumor growth of this group compared to the control groups (p<0.03).

These two experiments indicated that the vaccination with αGal$^{(-)}$ B16 cells is not able to treat pre-established subcutaneous melanoma tumors. On the other hand, pre-established subcutaneous melanoma tumors can be successfully treated by vaccination with αGal$^{(+)}$ B16 vaccines.

Survival Analysis of Mice with Pre-Established Subcutaneous Tumors Treated with αGal$^{(+)}$ B16 Vaccines Mice bearing pre-established αGal$^{(-)}$ B16 subcutaneous tumors vaccinated with αGal$^{(+)}$ B16 irradiated cells showed prolonged survival when compared with non-vaccinated controls and αGal$^{(-)}$ mock-vaccinated groups (FIG. 19). While zero out of 9 and only 1 out of 20 non-vaccinated and mock-vaccinated animals survived the subcutaneous challenge, respectively, 5 out of 19 mice treated with αGal expressing B16 cells survived for more than 70 days after the challenge. The median survival time for the no-vaccine and mock vaccine group were 27 and 26 days respectively. On the contrary, the median survival time of mice receiving αGal$^{(+)}$ B16 vaccines was significantly increased (39 days). This result demonstrates that αGal$^{(+)}$ B16 vaccines cells can efficiently treat pre-established subcutaneous melanoma tumors demonstrated by the increased number of surviving animals (26% vs. 5%) and by the prolonged median survival time (39 vs. 26 days).

In a second experiment mice received three doses of cell vaccines at 4, 11 and 18 days after the initial subcutaneous injection with non-irradiated αGal$^{(-)}$ B16 (FIG. 20). The vaccine dose each time was 3×10$^5$ cells. Mice were either not vaccinated (n=12), vaccinated with αGal$^{(-)}$ B16 (n=23) or vaccinated with αGal$^{(+)}$ B16 (n=26).

FIG. 20 shows the Kaplan-Meier survival analysis after 70 days of observation. The logrank test comparison of the survival curves indicated a significant difference in the number of surviving mice bearing subcutaneous melanoma tumors treated with αGal$^{(+)}$ B16 vaccines, compared to control non-vaccinated and αGal$^{(-)}$ B16 vaccinated mice (p<0.005). None out of 12 non-vaccinated mice survived the subcutaneous injection with B16. Similarly, none out of 23 mice vaccinated with αGal$^{(-)}$ B16 vaccines survived the subcutaneous injection with B16. On the contrary 11 out of 26 mice (42%)

receiving αGal$^{(+)}$ B16 vaccines survived for 70 days after the lethal subcutaneous injection of αGal$^{(-)}$ B16 melanoma.

The median survival of control and mock vaccinated mice were not significantly different (38 and 42 days, respectively, logrank test p=0.43, ns). On the contrary the median survival of mice treated with αGal$^{(+)}$ B16 was greater than 60 days. This represent a significant increase in the median survival of the αGal vaccinated group (p<0.005).

This result further demonstrated that the treatment of pre-established subcutaneous melanoma tumors with αGal$^{(+)}$ B16 vaccines is significantly effective in comparison to αGal$^{(-)}$ vaccination or no treatment.

Example 8

Treatment of Lung Melanoma Metastases by αGal$^{(+)}$ B16 Cell Vaccines

We further evaluated the efficacy in the treatment of lung melanoma metastasis as a model of disseminated disease. This experiment is very relevant from the clinical point of view since patients bearing tumors most likely will die from disseminated disease, which is surgically non-removable. Thus, RRBC-immunized mice were intravenously (i.v) challenged with $10^5$ non-irradiated αGal$^{(-)}$ B16 and randomized. Mice were treated subcutaneous with irradiated B16/NeoR vaccine (αGal$^{(-)}$, n=6) or with αGal$^{(+)}$ B16 vaccine (n=7). Vaccines ($2\times10^5$ irradiated cells) were administered subcutaneous at 4, 11 and 21 days after i.v. injection of B16 (FIG. 21). Mice were sacrificed 30 days after challenge and the number of melanoma metastasis were enumerated (FIG. 22). The number of lung metastasis were "too numerous to count" (arbitrary value>250 tumors) in 3 mice and 30 tumors were counted in the other mice, while only two mice were tumor free. Moreover, one of the animals in this group showed three additional metastatic nodules in the peritoneal cavity demonstrating dissemination of the disease in other places besides lungs.

On the contrary, mice treated with αGal$^{(+)}$ B16 vaccine were all tumor free demonstrating that pre-established tumor were treated very successfully by the αGal$^{(+)}$ expressing vaccine therapy.

In a second independent experiment (FIG. 23) a five-fold increase dose escalation of non-irradiated αGal$^{(-)}$ B16 was used. Mice were injected i.v. with $5\times10^5$ live B16 to pre-establish the lung melanoma metastases. Four days later vaccination with control and αGal$^{(+)}$ B16 cells was performed as before. Mice received either no vaccine treatment (n=10), three doses of αGal$^{(-)}$ B16 (n=11) or αGal$^{(+)}$ B16 vaccines (n=11).

Thirty days after the i.v. challenge with B16, mice were euthanized and lung melanoma metastases enumerated (FIG. 23). Also the tumor growth was evaluated by counting the lung tumor burden and by weighting lung tissue (FIG. 24).

Numerous lung melanoma metastases were found in the lungs of non-vaccinated mice as well as in the control vaccinated group. To perform statistic comparisons, the weight of lung tissue was used. The difference between the lung burden in control and non-vaccinated groups was not statistically different (Unpaired t Test p=0.66, ns). On the contrary, significantly reduced lung burden was observed in mice vaccinated with αGal expressing B16 vaccines (One way ANOVA p<0.006).

Similar to the observations of the first experiment, some mice from control and no-vaccine group had "too numerous to count" melanoma metastases. In addition, two animals had scattered melanoma tumors extra-pulmonary, indicating disseminated disease in addition to pulmonary tissue. None of the αGal$^{(+)}$ B16 vaccinated mice had "too numerous to count" melanoma tumors in the lungs and none had extra-pulmonary tumors. This indicates that vaccination with αGal$^{(+)}$ B16 vaccines can effectively treat disseminated metastatic melanoma. In addition, the vaccination with αGal$^{(+)}$ B16 vaccines can prevent further spreading of the systemic disease.

Example 9

T Cell Studies to Demonstrate Induction of αGal$^{(-)}$ B16-Specific T Cell Precursors after Vaccination with αGal$^{(+)}$ B16 Cells One of the fundamental questions of this technology is whether the vaccination with αGal$^{(+)}$ cells will induce T cell mediated immunity capable to react against the αGal$^{(-)}$ tumor. In the experiments shown above we demonstrated that αGal$^{(+)}$ B16 vaccines induce strong immunity able to mediate the clearance of pre-established αGal$^{(-)}$ tumors. This immunity in not induced when mice are vaccinated with αGal$^{(-)}$ B16 vaccines. To further demonstrate that T cell precursors specific for the αGal$^{(-)}$ B16 tumors were induced after vaccination with αGal$^{(+)}$ B16 vaccines, in vitro T cell studies were conducted. The goal of these experiments was to demonstrate specific recognition of the αGal$^{(-)}$ B16 cells by T cells. T cells were harvested from mice vaccinated with control vaccine αGal$^{(-)}$ B16 group or from mice vaccinated with αGal$^{(+)}$ B16 irradiated cells (FIG. 25). Two types of studies were performed that demonstrated by different means the same conclusion, that is, that mice vaccinated with irradiated αGal$^{(+)}$ B16 cell have increased numbers of T cell precursors able to recognize specifically αGal$^{(-)}$ B16 tumor cells.

In the first set of experiments, the intracellular cytokine TNF-α was detected by FACS. Cells harvested from mice vaccinated with irradiated αGal$^{(-)}$ B16 cells or with αGal$^{(+)}$ B16 cells, two weeks after the last subcutaneous vaccination. Splenocytes were cultured without stimulation as negative control. For stimulation, they were co-cultured with CA320M (αGal$^{(-)}$ syngeneic H-2 b/b haplotype) as negative control or with αGal$^{(-)}$ B16 cells. After 6 hours of stimulation cells were harvested and stained for intracellular TNFα. Increased percentage of TNFα$^{(+)}$ lymphocytes was found in the spleens of mice vaccinated with αGal$^{(+)}$ B16 cells that specifically recognized αGal$^{(-)}$ B16 cells (FIG. 26). These T cells did not produce TNFα when cultured with CA320M which indicates that they specifically recognize B16 and not a non-related syngeneic cell line. In addition to the increased number of melanoma specific T cell precursors, the quantitative amount of TNFα produced by these cells was significantly increased measured by the Mean fluorescence intensity detected by FACS (FIG. 26). Four-fold increased MFI in the TNFα$^{(+)}$ cells was detected. When splenocytes from mock-vaccinated mice were cultured with αGal$^{(-)}$ B16, only 4% of TNFα$^{(+)}$ cells were detected with a MFI of 17. On the contrary, when T cells from mice receiving αGal$^{(+)}$ B16 cell vaccines were cultured with αGal$^{(-)}$ B16, 7% of TNFα$^{(+)}$ cells were detected with a MFI of 69. This represents a two fold increase in the percentage of T cell precursors present in the spleen. This experiment was repeated a total of three times and similar results were obtained.

This result demonstrated that the vaccination with αGal$^{(+)}$ B16 cells and not vaccination with αGal$^{(-)}$ B16 induces a strong specific T cell immunity detected in vitro by T cell specific recognition of the melanoma target.

In a different set of experiments, cell-surface activation markers were used to measure specific T cell recognition of the αGal$^{(-)}$ B16 melanoma cell line. It is well described that upon engagement of the T cell receptor (TCR), T cells up-regulate several cell surface molecules that indicate an activated state of the lymphocyte. One of those molecules is the IL-2 receptor alpha chain or CD25. Upon TCR engagement, CD25 is up-regulated and can be detected by FACS at 1 day after activation. Similarly, CD69 (or very early activation antigen (VEA)) is up-regulated upon T cell activation. CD69 functions as a signal-transmitting receptor in different cells, it is involved in early events of lymphocyte activation and contributes to T cell activation by inducing synthesis of different cytokines, and their receptors. Both activation markers (CD25 and CD69) are expressed at very low level in resting T cells. To demonstrate that vaccination with αGal$^{(+)}$ B16 cells induced T cell precursors able to recognize specifically αGal$^{(-)}$ B16, the up-regulation of activation markers was used as parameters to measure recognition and activation. Cells were harvested from mice vaccinated with αGal$^{(-)}$ B16 or vaccinated with αGal$^{(+)}$ B16. They were cultured without stimulation or stimulated with a negative control cell line (CA320M) or with αGal$^{(-)}$ B16. After 24 hours of culture, cell were harvested and stained to detect CD25 or CD69. Acquisition was performed gating in cells excluding the vital staining 7-AAD (live cells). As expected, resting T cells (no stimulation) and cells stimulated with the syngeneic non-melanoma cell line CA320M expressed very low levels of activation markers (FIGS. 27a and 27b). When splenocytes from mice receiving αGal$^{(-)}$ B16 were cultured with B16, some up-regulation of activation markers was observed. This corroborate previous reports from the literature which indicated that low-degree of immune reactivity can be observed when mice receive native αGal$^{(-)}$ B16 vaccines. However this reactivity is not sufficient to prevent and or treat pre-established melanoma tumors. On the other hand, increased activation of lymphocytes from mice vaccinated with αGal$^{(+)}$ B16 was detected when T cells were cultured with αGal$^{(-)}$ B16, as increased number of CD25$^{(+)}$ and CD69$^{(+)}$ cells were measured.

This result once again demonstrated that vaccination with αGal$^{(+)}$ B16 cells induced T cell precursors able to recognize specifically αGal$^{(-)}$ B16 melanoma cells.

Example 10

Treatment of Pre-Established Metastatic Melanoma Tumors by Adoptive T Cell Transfer from Mice Vaccinated with αGal$^{(+)}$ or αGal$^{(-)}$ B16 Cell Vaccines The in vitro experiments shown above demonstrated that more quantity and quality of melanoma specific T cells are induced in mice vaccinated with αGal$^{(+)}$ B16 cells when compared to mice receiving αGal$^{(+)}$ B16 vaccination. These melanoma specific T cells were increased in numbers (more T cells found in spleens) and they produced more TNFα. Also, more splenocytes were activated when co-cultured with B16 (up-regulation of CD25 and CD69). In experiments shown before, mice bearing both subcutaneous and lung pulmonary metastasis receiving αGal$^{(+)}$ B16 showed prolonged survival and increased clearance of the lung tumors. Having these two groups of data, we could infer that in fact T cells induced by αGal$^{(+)}$ B16 vaccination are responsible for the treatment of pre-established melanoma tumors. However, it is not obvious that this is the case since it has been shown that large amount of melanoma-specific T cells are insufficient to treat pre-established subcutaneous melanoma tumors, since they are in a tolerant state [Overwijk et al. "Tumor regression and autoimmunity after reversal of functionally tolerant state of self-reactive CD8+T cells" J. Exp. Med. (2003) 198: 569-580]. We hypothesized that vaccination with αGal$^{(+)}$ B16 cells induced a strong cell mediated immunity that can be rapidly activated upon recall and it is responsible for tumor clearance in mice bearing pre-established disease. To demonstrate this hypothesis adoptive cell transfer experiments were conducted (FIG. 28). Donor mice were vaccinated receiving three doses of irradiated αGal$^{(+)}$ B16 or αGal$^{(-)}$ B16 vaccines as described before. Recipient mice were i.v injected with live αGal$^{(-)}$ B16 to establish the lung melanoma metastasis and randomized. Four days after i.v injection of non-irradiated B16, mice received, or not T cells from donors vaccinated with αGal$^{(+)}$ or αGal$^{(-)}$ B16 cells. Four weeks later, the lung melanoma metastasis burden was measured by enumerating lung tumors, and by weighting lungs obtained in block. The experiment was performed twice and results from both are depicted in FIGS. 29A and 29B. Experiment #1 shows the average lung weight of mice receiving i.v B16 with no T cell therapy (n=16), mice receiving T cells from αGal$^{(-)}$ B16 vaccinated mice (n=15) and mice receiving T cells from mice vaccinated with αGal$^{(+)}$ B16 (n=17). The bars represent the average in lung weight and error bars, the SEM. Large tumors and significant increased lung burden was demonstrated in control mice and in mice receiving T cells from mock-vaccinated mice. The difference in lung melanoma metastasis between mice receiving no T cells (control) and mice receiving T cells from mock-vaccinated mice was found not statistically different (p>0.05). On the contrary significant reduction of the lung melanoma burden was observed in mice receiving T cells from αGal$^{(+)}$ B16 vaccinated mice (One-way ANOVA p<0.05). Similar results were observed in a second independent experiment. Mice receiving no T cells have an average of 64 lung melanoma tumors (n=7). Mice receiving cells from αGal$^{(+)}$ B16 vaccinated mice had as many lung melanoma metastasis (mean=90, n=10, p=>0.05). In contrast, an average of only 31 lung melanoma tumors were observed in mice receiving splenocytes from mice vaccinated with αGal$^{(+)}$ B16 cells. This represents a significant reduction in the lung melanoma burden of mice receiving T cells from αGal$^{(+)}$ B16 vaccinate mice (Unpaired t Test p<0.05).

This remarkable success in the reduction of pre-established lung melanoma metastasis with the sole treatment of cells from αGal$^{(+)}$ vaccinated mice, demonstrates for the first time that strong cell mediated immunity is induced by αGal$^{(+)}$ cell vaccines and not with αGal$^{(-)}$ vaccines. This strong cell dependent tumor immunity is, with little doubt, responsible for the treatment of disseminated pre-established disease.

Example 11

Survival of αGal$^{(-)}$ Knockout Mice Vaccinated with αGal$^{(-)}$ or αGal$^{(+)}$ Irradiated CA320M Sarcoma Cells after Subcutaneous Injection of a Lethal Dose of Non-Irradiated αGal$^{(-)}$ CA320M Cells The prophylactic vaccination experiments described above with B16 melanoma cells were repeated with a different tumor cell line derived from the αGal$^{(-)}$ knockout mice and therefore are completely syngeneic with the host. This cell line is CA320M and was obtained by intraperitoneal injection of 2 mg 9,10-dimethyl-1,2-benz-anthracene (DMBA) and 1 mg 3-methylcholanthrene (3-MC) dissolved in 250 µl of olive oil at two week intervals into αGT knockout mice. One mouse presented a tumor eight months after the first injection. The tumor was localized to the intraperitoneal cavity with a large mass approximately 2 cm wide by 3 cm tall and 1.5 cm deep. Metastatic nodules located on the mesenteries were noted. Both the primary mass and the intestinal tract were collected for culture and histopathological examination. Metastatic nodules collected from the mesenteries associated with the primary site of tumor were successfully cultured and designated CA320M. Histopathological examination of both frozen and paraffin sections of the primary and transplanted tumors, respectively, demonstrated morphologies consistent with a poorly differentiated sarcoma. Hematoxylin and eosin staining along with immunohistochemical analysis suggests that CA320M can be classified in the family of gastrointestinal stromal tumors as a sarcoma of the small intestine. CA320M cells induced in a αGT KO mouse failed to bind $IB_4$ isolectin that specifically detects αGal epitopes, verifying that this murine tumor is, as expected, devoid of functional αGT enzyme and, therefore, αGal epitopes. CA320M cells were susceptible to infection by an HSV-1 based vector and expressed αGal epitopes after transduction with HE7αGal1.

αGT KO mice were primed to develop immunity against the αGal epitope by subcutaneous injection of $2 \times 10^7$ rabbit whole blood cells twice at 14 day intervals. CA320M cells were transduced with 10 MOI of either HDKgal or HDKgalΔ-salI for eight hours to obtain CA320M αGal$^{(+)}$ or αGal$^{(-)}$ cells, respectively. Briefly, HDKgal was developed by inserting the αGT gene with a Kozak sequence into the pHD1 amplicon HSV-1 vector. pHDKgal therefore carries a single eukaryotic gene, αGT, under the control of the CMV promoter. To construct the mutant αGT gene, a unique SalI restriction site, located in the corresponding catalytic domain of the αGT enzyme, was cut and filled in using Klenow and dNTP's. The resulting frameshift mutation yields premature termination of the polypeptide rendering the enzyme non-functional. The mutant αGT gene was also cloned into the pHD1 amplicon and both amplicons were packaged into infectious HSV virions using a helper-free herpes viral system. Transduced CA320M cells were irradiated (25 Gy) and $1 \times 10^3$ cells injected into each of 15 animals. Twenty-one days later animals were challenged with $1 \times 10^7$ live CA320M cells and followed for tumor growth and survival analysis. Ninety-three percent of αGal$^{(+)}$ CA320M vaccinated animals survived lethal tumor challenge for up to 60 days (>400 mm$^3$ tumor) compared to animals vaccinated with the mutant αGal$^{(-)}$ CA320M (33%) and null (38%) controls (FIG. 30). This results confirms that vaccination with αGal$^{(+)}$ syngeneic cells is capable to induce a protective immune response against the corresponding αGal$^{(-)}$ cells.

Taking together, all these results demonstrate for the first time that the presence of α-Galactosyl epitopes in whole cell vaccines represent a strong immune adjuvant able to induce T cell mediated immunity to treat pre-established tumors lacking the expression of αGal epitopes. These results also indicate that clinical use of this vaccine may have a significant impact in human medicine. In addition, the preventive vaccination for cancer patients currently is not possible consequently therapeutic approaches like the technology described here have a realistic value for the rapid application and possible benefit of cancer patients.

Example 12

Development of Human Whole Cell Cancer Vaccine (HyperAcute™)

Hyperacute™ whole cell cancer vaccines consists of allogeneic cancer cell lines genetically engineered to express murine α(1,3)galactosyltransferase gene. Several independent cancer cell lines from several tumor tissue types have been engineered to express αGal epitopes on their surface. A therapeutic whole cell cancer vaccine consists of injection of irradiated individual cell lines or a mixture of several engineered cancer cell types belonging to the same tumor tissue type. Table 1 indicates the cancer cell lines that were used to originate the HyperAcute™ whole cell cancer vaccines.

TABLE 1

HyperAcute ™ whole cell cancer vaccines

| Hyper Acute ™ Vaccine | Cell Line | ATCC # | Tumor Tissue Type | Description |
|---|---|---|---|---|
| HAL1 | A549 | CCL-185 | lung | carcinoma |
| HAL2 | NCI-H460 | HTB-177 | lung | large cell carcinoma |
| HAL3 | NCI-H520 | HTB-182 | lung | squamous cell carcinoma |
| HAB1 | MCF-7 | HTB-22 | breast | pleural effusion adenocarcinoma |
| HAB2 | BT-20 | HTB-19 | breast | carcinoma |
| HAPA1 | HPAF-II | CRL-1997 | pancreas | ascitis adenocarcinoma |
| HAPA2 | PANC-1 | CRL-1469 | pancreas | primary ductal epithelial carcinoma |
| HAPA3 | ASPC-1 | CRL-1682 | pancreas | metastatic adenocarcinoma |
| HAPA4 | BxPC3 | CRL-1687 | pancreas | primary adenocarcinoma |
| HAO1 | IGROV | NA | ovary | carcinoma |
| HAO2 | ES-2 | CRL-1978 | ovary | clear cell carcinoma |
| HAO3 | NIH:OVCAR3 | HBT-161 | ovary | ovarian adenocarcinoma |
| HAO4 | PA-1 | CRL-1572 | ovary | ovarian teratocarcinoma |
| HAM1 | A375 | CRL-1619 | melanoma | malignant melanoma |
| HAM2 | COLO829 | CRL-1974 | melanoma | malignant melanoma |
| HAM3 | G-361 | CRL-1424 | melanoma | malignant melanoma |
| HAC1 | HCT-116 | CCL-247 | colon | colorectal carcinoma |
| HAC2 | COLO205 | CCL-222 | colon | metastatic adenocarcinoma |
| HAC3 | LoVo | CCL-229 | colon | metastatic adenocarcinoma |
| HAC4 | WiDr | CCL-218 | colon | colorectal adenocarcinoma |
| HAC5 | DLD-1 | CCL-221 | colon | colorectal adenocarcinoma |
| HAC6 | HCT-15 | CCL-225 | colon | colorectal adenocarcinoma |
| HAC7 | SW620 | CCL-227 | colon | metastatic adenocarcinoma |
| HAC8 | SW480 | CCL-228 | colon | metastatic adenocarcinoma |
| HAC9 | SW1116 | CCL-233 | colon | colorectal adenocarcinoma grade II |
| HAC10 | HT-29 | HTB-38 | colon | colorectal adenocarcinoma grade II |
| HAC11 | FHC | CRL-1831 | colon | normal mucosal colon |
| HAC12 | CCD841CoN | CRL-1790 | colon | normal colon |
| HAPR1 | PC-3 | CRL-1435 | prostate | metastatic adenocarcinoma |
| HAPR2 | LNCaPFGC | CRL-1740 | prostate | metastatic adenocarcinoma |
| HAPR3 | MDAPca2b | CRL-2422 | prostate | metastatic adenocarcinoma |
| HAPR4 | DU145 | HTB-81 | prostate | metastatic carcinoma |

HyperAcute™ whole cell cancer vaccines were established by transduction of the cell lines indicated in Table 1 with retroviral supernatant from 293Z.CKG in the presence of protamine sulfate 10 μg/mL. The population of transduced cells was stained for αGal cell surface epitopes using 0-2605 anti-αGal antibody (NewLink). Five percent of the cell population with the highest intensity of αGal epitopes expression on their cell surface was sorted into a separate subpopulation using FACS sorter. The sorted subpopulation of transduced cells with highest expression of αGal epitopes was the one designated as indicated in Table 1. These cells were expanded (split ratio 1:5) to generate a master cell bank (MCB). Growth pattern, morphologic appearance and mean intensity of αGal epitopes expression have been monitored and remained stable during the whole period of propagation in culture. MCB were developed by expanding the cells in flasks at 37° C.±1° C. in 5%±1% CO2. The culture medium was RPMI-1640 supplemented with 10% fetal bovine serum (FBS) and 2 mm L-glutamine. At each passage the cells were trypsinized, counted and their viability was assessed by trypan blue exclusion. Cells were propagated to provide one billion cells, harvested, pooled, distributed into 100 cryovials, and frozen using programmed rate freezing chamber. Cells are stored in the vapor phase of liquid nitrogen storage tank. A working cell bank (WCB) for each cell line was developed from a MCB. Conditions for WCB expansion, harvesting, freezing and storage were as it is described for MCB. A production lot for each HyperAcute™ cancer cell line was originated from each WCB. When the cells from the production lot reach sufficient density, the culture fluids (supernatant) are harvested, filtered, and pooled into a sterile container. The pool is thoroughly mixed and then aseptically filled into labeled, sterile plastic bottles. (Labels contain the product name, lot number and date of filling). The fill bottles are frozen and stored at or below −60° C. Aliquots are submitted for safety testing. Cells for a Production Lot are harvested by trypsinization, pooled, and resuspended in complete culture medium. Pooled cells are irradiated at 150-200 Grey. The cells were irradiated using a Varian Clinic 2100C medical linear accelerator operating in the 6MV photon mode. The machine's radiation output is calibrated in water using the AAPM TG-51 calibration protocol. Output consistency is monitored daily; and output calibration is checked monthly with a NIST calibration traceable ion chamber/electrometer dosimeter. Irradiated cells are centrifuged and resuspended in final formulation for injection consisting of 5% glycerol and human serum albumin. Then 0.4 ml of cells at concentrations of $1\times10^6/0.2$ ml, $3.5\times10^6/0.2$ ml, $1\times10^7/0.2$ ml and $3.5\times10^7$ cells/0.2 ml corresponding to dose levels I, II, III and IV are distributed into sterile cryovials. The HyperAcute™ cells MCB, WCB, and PL quality control testing involves both cells and supernatant. Acceptance criteria for HyperAcute™ cancer vaccine MCB, WCB and PL cells consist in assays for tumorigenicity in nude mice.

Example 13

Dose Levels and Dosing Schedule for Human Patients

The following data support proposed dose levels and vaccination schedule. Pre-clinical toxicology studies in mice have shown that α-gal expressing allogeneic and syngeneic tumors are well tolerated up to $1\times10^6$ cells per mouse which is equivalent to $3.5\times10^9$ cells per 70 kg human. Phase I study with murine vector producer cells (see Section 2.1) naturally expressing α-gal epitopes on cell surface has shown that murine VPC were well tolerated at the dose $7\times10^9$ cells per patient. In Phase II murine VPC trial a patient has undergone three cycles of treatment with $7\times10^9$ cells injected in each cycle. The patient tolerated the treatment well. Murine VPC injections were repeated with an interval of 6 weeks. The proposed dose levels are within well-tolerated doses of α-gal vaccine in mice (maximum $4\times10^8$ cells per patient). Four week intervals between vaccine injections will allow sufficient time for evaluation of toxicity of the treatment and for maturation of the immune response. Data from Phase I murine VPC study suggest that anti-αGal immune response reaches its maximum between 14 and 21 days after αGal expressing cells injection.

Example 14

Toxicology Studies Using Syngeneic Tumor Vaccines Transduced with Retroviral Vector Carrying Murine αGT Gene In a first study, mice were injected subcutaneously with αGal$^{(+)}$ B16 melanoma cells at a dose of 1 $10^5$ cells per mice. Animals that rejected αGal$^{(+)}$ living melanoma cells were re-challenged with αGal$^{(-)}$ B16 cells to prove that the rejection of αGal$^{(+)}$ melanoma cells induced tumor immunity. All mice survived the second challenge with B16. These melanoma-protected animals (n=8 in the first experiment and n=9 in the second experiment) were followed for long term toxicity studies for a period of six months. Histological, hematological, clinical observations for toxicity studies have been performed with some of the protected mice. Histopathological examinations included major perfused organs: kidney, spleen and liver, as well as potential target tissue, skin and mammary gland. Histological studies evaluating safety indicated no remarkable lesions in all sample tissues examined (skin, mammary gland, kidney, spleen, liver). Some animals (that included control mice) showed renal perivasculitis with minimal infiltrates of inflammatory cells. The frequency of this observation in the test group was similar to the frequency in the control group of animals. Hematology results showed all values studied were within the range of normal values. Normal values were considered results from naïve un-manipulated α-gal KO mice Clinical observations including behavior, and the development of autoimmune depigmentation (vitiligo) or fur changes, as a secondary possible adverse event were not observed during the period of study in melanoma protected mice (n=17).

In a second study, mice were injected subcutaneously with allogeneic αGal$^{(+)}$EMT-6 breast cells at a dose of $1\times10^6$ cells per mouse. Two, four and six weeks after vaccination, blood and tissue samples were obtained to perform toxicology studies. Histological and hematological toxicity studies were performed. Histopathology examinations included major perfused organs: kidney, spleen and liver, as well as potential target tissue, skin and mammary gland. Histological studies evaluating safety indicated no remarkable lesions in all sample tissues examined (skin, mammary gland, kidney, spleen, liver). Some animals (that included control mice) showed renal perivasculitis with minimal infiltrates of inflammatory cells. The frequency of this observation in the test group was similar to the frequency in the control group of animals. Hematology results showed all values studied were within the range of normal values. Normal values were considered results from naïve un-manipulated α-gal KO mice. Transient eosinophilia was observed at two weeks after allogeneic vaccination. The maximal dose used in the toxicology studies was $1\times10^6$ cells/mouse. Scaling of this dose to humans based on the dose/kg, assuming that a mouse is 20 grams, shows that the dose/mouse is equivalent to $3.5\times10^9$ cells in a 70 kg human. Also considering that the average life span of a mouse is about 2 years compared to an average of 70 years for humans, the long-term toxicity study (6 months) would be equivalent to one quart of a mice life span, which are about 17 humans years. These studies support the current dose-schedule $4 \times 10^8$ per patient over a 16-week treatment period.

Example 15

Preparation and Schedule of Administration of HyperAcute™ Cancer Vaccine to Patients This procedure describes how to prepare and administer to human patients the whole cell cancer vaccine (the pharmaceutical composition of the invention). Cells should be injected into patients immediately after they have been prepared. No specific safety precautions are necessary because administered cells have been lethally irradiated before freezing. First, the cryovials of each vaccine cell line are retrieved from the liquid nitrogen container. Then, all the vials are thawed simultaneously by immersing in the water bath at 37° C. to above the frozen content level. As soon as vials are thawed, rinse their surface with 70% alcohol. Equal amounts of content of vial(s) with each cell line component of the vaccine are combined into one syringe for injection and immediately injected into the patient. The vaccine cells will be injected intradermally (i.d.) using a tuberculin syringe with a 25-gauge needle. Injections should be given in the arms and legs on a rotating basis. HyperAcute™ (HAL, HAB, etc.) vaccine cells will be administered on days 1, 29, 57, and 85. Patients will be monitored for two hours after each injection in the outpatient clinic by the nursing staff. Patient monitoring is to include: Temperature (T), pulse (P), blood pressure (BP) and respiratory rate (R), within 30 minutes before administration of the vaccine, and then by checking every 15 minutes×4, then every 30 minutes×2 after the vaccination. Temperature will be checked prior to discharge from the clinic. In addition, patients will be monitored for signs of acute reactions including local or disseminated skin rash and other adverse reactions. Patients experiencing Grade II or greater acute adverse events may be monitored for an additional 1-2 hours in the clinic until the event has resolved to less than Grade II. If an AE of Grade II or greater persists for more than 4 hours despite observation and/or treatment, a decision on whether to continue observation, institute or modify treatment, or admit the patient to the hospital

Example 16

Determination of Maximum Tolerated Dose

Treatment will proceed in dose cohorts of 3 eligible patients. The maximum tolerated dose (MTD) is defined as the dose cohort below that at which dose-limiting toxicity (DLT) is seen. If >33% of patients (i.e., ⅓, or 2/4-6) in a dose cohort manifest DLT, then the MTD will have been determined and further dose escalations will not be permitted. If DLT is noted in one of three patients (⅓) in a dose cohort, then that cohort will be expanded to accrue up to a total of six (6) patients. If another DLT is observed, the cohort will be closed, MTD will be defined and no further dose escalation permitted. If no other DLT is observed in the cohort, accrual to the next higher dose cohort will be initiated. Further patients will be treated on the Phase II portion of the study at the MTD.

There will be a minimum delay of 4 weeks between the entry of the last patient on a dose cohort and the entry of the first patient on the next higher dose cohort.

TABLE 2

Treatment Plan

| Cohort | Pts. (N = 3) | Vaccine HAL Cells |
|---|---|---|
| A | 3 | $3 \times 10^6$ |
| B | 3 | $1 \times 10^7$ |
| C | 3 | $3 \times 10^7$ |
| D | 3 | $1 \times 10^{8}$* |

*Injection site may be split due to number/volume of cells used.

Response and progression is evaluated in this study using the new international criteria proposed by the Response Evaluation Criteria in Solid Tumors (RECIST) Committee. Changes in only the largest diameter (unidimensional measurement) of the tumor lesions are used in the RECIST criteria. Lesions are either measurable or non-measurable using the criteria provided below. The term "evaluable" in reference to measurability will not be used because it does not provide additional meaning or accuracy. Measurable lesions are defined as those that can be accurately measured in at least one dimension (longest diameter to be recorded) as ≥20 mm with conventional techniques (CT, MRI, x-ray) or as ≥10 mm with spiral CT scan. All tumor measurements must be recorded in millimeters (or decimal fractions of centimeters). All other lesions (or sites of disease), including small lesions (longest diameter <20 mm with conventional techniques or <10 mm using spiral CT scan), are considered non-measurable disease. Bone lesions, leptomeningeal disease, ascites, pleural or pericardial effusions, lymphangitis cutis or pulmonis, inflammatory breast disease, abdominal masses (not followed by CT or MRI), and cystic lesions are all considered non-measurable. All measurable lesions up to a maximum of five lesions per organ and 10 lesions in total, representative of all involved organs, should be identified as target lesions and recorded and measured at baseline. Target lesions should be selected on the basis of their size (lesions with the longest diameter) and their suitability for accurate repeated measurements (either by imaging techniques or clinically). A sum of the longest diameter (LD) for all target lesions is calculated and reported as the baseline sum LD. The baseline sum LD will be used as reference by which to characterize the objective tumor response. All other lesions (or sites of disease) should be identified as non-target lesions and should also be recorded at baseline. Non-target lesions include measurable lesions that exceed the maximum numbers per organ or total of all involved organs as well as non-measurable lesions. Measurements of these lesions are not required but the presence or absence of each should be noted throughout follow-up. All measurements should be taken and recorded in metric notation using a ruler or preferably calipers. All baseline evaluations should be performed as closely as possible to the beginning of treatment and never more than 2 weeks before the beginning of the treatment. Tumor lesions that are situated in a previously irradiated area are not considered measurable. Clinical lesions are only be considered measurable when they are superficial (e.g., skin nodules and palpable lymph nodes). In the case of skin lesions, documentation by digital color photography, including a ruler to estimate the size of the lesion, is recommended. Lesions on chest x-ray are acceptable as measurable lesions when they are clearly defined and surrounded by aerated lung. However, CT is preferable. Conventional computed tomography (CT) and magnetic resonance imaging (MRI) should be performed with cuts of 10 mm or less in slice thickness contiguously. Spiral CT should be performed using a 5 mm contiguous reconstruction algorithm. This applies to tumors of the chest, abdomen, and pelvis. Head and neck tumors and those of extremities usually require specific protocols. Ultrasound (US) is utilized when the primary endpoint of the study is objective response evaluation. US should not be used to measure tumor lesions. It is, however, a possible alternative to clinical measurements of superficial palpable lymph nodes, subcutaneous lesions, and thyroid nodules. US might also be useful to confirm the complete disappearance of superficial lesions usually assessed by clinical examination. Endoscopy and Laparoscopy is for objective tumor evaluation has not yet been fully and widely validated. Their uses in this specific context require sophisticated equipment and a high level of expertise that may only be available in some centers. Therefore, the utilization of such techniques for objective tumor response should be restricted to validation purposes in reference centers. However, such techniques can be useful to confirm complete pathological response when biopsies are obtained. Tumor markers-alone cannot be used to assess breast tumor response. Cytology and histology can be used to differentiate between partial responses (PR) and complete responses (CR) in rare cases (e.g., residual lesions in tumor types such as germ cell tumors, where known residual benign tumors can remain). Cytopathological confirmation of the neoplastic origin of any effusion that appears or worsens during treatment when measurable tumor has met the criteria for response or stable disease is mandatory to differentiate between response or stable disease (an effusion may be a side effect of the treatment) and progressive disease.

Example 17

Phase I/II Study of an Antitumor Vaccination Using α(1,3)galactosyltransferase Expressing Allogeneic Tumor Cells in Patients with Refractory or Recurrent Non-Small Cell Lung Cancer (NSCLC)

Lung cancer remains the leading cause of cancer death. In a phase I/II trial, we examined the safety and feasibility of antitumor vaccination in patients with advanced non-small cell lung cancer (NSCLC) with genetically altered allogeneic human lung cancer cells engineered to express xenotransplantation antigens by retroviral transfer of the murine α(1, 3)galactosyltransferase gene (HyperAcute™ Lung Cancer Vaccine). Patients with stage IV, recurrent or refractory NSCLC, ECOG PS ≤2, prior chemotherapies ≤2, adequate bone marrow and organ function, and albumin ≥3.0 g/dL were eligible. Cohorts of 3 patients each were scheduled to receive 4 doses of intradermal injections of 3, 10, 30, or 100 million vaccine cells every 4-weeks. HyperAcute™ Lung Cancer Vaccine consisted in a mixture of equal number of gamma-irradiated cell lines HAL1, HAL2 and HAL3. Toxicity was assessed using the CTC v3.0 and response determined by RECIST criteria. To date, 7 patients, 5 males, 2 females, median age 56 yrs (range, 41-72), median number of prior chemotherapies=1 (range, 1-2) were treated. Four patients have received 4/4 vaccinations, 2 patients received 3 vaccinations and 1 patient received 2 vaccinations. Adverse events (≤CTC grade 2) definitely, probably or possibly attributable to the vaccine include injection site pain/discomfort, local skin reaction, fatigue, and hypertension. Other adverse events (≤grade 2) include bradycardia, cough, diarrhea, dyspnea, headache, hyperglycemia, hyponatremia, nausea, pleural effusion, and vomiting. To date no Grade 3 or 4 adverse events attributed to the vaccine have been observed. One patient had cough syncope (grade 3) that was not related to the vaccine. Table 1 shows a synopsis of the patients, adverse events and response to date. One patient treated at the lower dose showed progression of the disease and voluntarily dropped off the study before receiving all 4 doses of the vaccine. Two patients with stage IIIA of non-small cell lung cancer (NSCLC) that received all four doses of the lower dose of vaccine (3 million cells per dose) showed stable disease after 7 months of vaccination. Similarly, two patients with stage IIIB and IV NSCLC, in the second cohort of patients that received all 4 doses of the vaccine (10 million cells per dose) also showed stabilization of the disease at 4 months after starting vaccination. Only one patient with stage IV disease has been treated in the third cohort of patients (2 doses of 30 million cells) so far, showing no adverse effects. In total, four patients had stable disease for >16 weeks (range, 17-28 weeks). The median survival of Stage IV NSCLC subjected to several chemotherapeutic regimens is 5.5 to 8 months and patients generally show progressive disease during this period. Current treatments have limited impact on outcome. Data of the current Phase I/II clinical trial indicate that vaccination of patients with stage III-IV NSCLC with Hyper-Acute™ lung cancer vaccines is safe, feasible and more effective than historical chemotherapeutic treatment controls or historical untreated controls, as stabilization of the disease was achieved after 4 doses of vaccination in 80% of the patients treated so far.

From the foregoing it can be seen that the invention accomplishes at least all of its objectives. All references cited herein are hereby incorporated in their entirety.

TABLE 1

NLG0101-HyperAcute ™-Lung Cancer Vaccine Trial, IND#11261: Summary of Patients, Results and Adverse Events

| Patient No. | Age (Yrs.) | Sex (M/F) | NSCLC Initial Stage | HAL Vaccine Cells per Dose | Date on Study/No. Vaccines | Grade/Adverse Event | Response |
|---|---|---|---|---|---|---|---|
| 1 | 41 | M | IIIB | 3 million | 20 Apr. 2004/ 3/4 vaccinations *Voluntarily came off study after 3rd dose. | Grade 1 Fatigue Grade 1 Bradycardia Grade 1 Hyperglycemia Grade 1 Cough Grade 1 Nausea Grade 2 Vomiting Grade 2 Pleural effusion Grade 1 Injection site reaction | Progressive Disease CNS metastases at 5 months |
| 2 | 58 | M | IIIA | 3 million | 22 Apr. 2004/ 4/4 vaccinations | Grade 1 Hyperkalemia Grade 1 Cough Grade 1 Dyspnea Grade 1 Fatigue Grade 1 CPK Grade 1 Injection site reaction | Stable Disease |

TABLE 1-continued

NLG0101-HyperAcute ™-Lung Cancer Vaccine Trial, IND#11261: Summary of Patients, Results and Adverse Events

| Patient No. | Age (Yrs.) | Sex (M/F) | NSCLC Initial Stage | HAL Vaccine Cells per Dose | Date on Study/No. Vaccines | Grade/Adverse Event | Response |
|---|---|---|---|---|---|---|---|
| 3 | 70 | M | IIIA | 3 million | 27 May 2004/ 4/4 vaccinations | Grade 1 Injection site reaction<br>Grade 2 Hyperglycemia<br>Grade 1 Diarrhea | Stable Disease |
| 4 | 49 | F | IIIB | 10 million | 15 Jul. 2004/ 4/4 vaccinations | Grade 1 Diarrhea<br>Grade 2 Headache<br>Grade 1 Injection site reaction<br>Grade 1 Hypocalcaemia<br>Grade 1 Hyponatremia<br>Grade 1 Hypercholesterolemia | Stable Disease |
| 5 | 56 | F | IV | 10 million | 12 Aug. 2004/ 4/4 vaccinations | Grade 1 Injection site reaction (acute)<br>Grade 2 Pain, skin<br>Grade 1 Pain- muscle | Stable Disease |
| 6 | 49 | M | IV | 10 million | 09 Sep. 2004/3 vaccinations to date | Grade 1 Injection site Reaction<br>Grade 3 Cough (tussive) syncope | Not Assessed Yet |
| 7 | 72 | M | IV | 30 million | 14 Oct. 2004/2 vaccinations to date | None | Not Assessed Yet |

What is claimed is:

1. A pharmaceutical composition comprising a tumor cell preparation obtained from a human tumor cell line, each cell comprising a plurality of cell surface glycoproteins on which an αGal epitope is present, wherein αGal epitopes are present in an amount effective to treat a preexisting tumor, suspended in a pharmaceutically acceptable carrier suitable for injection in human patients, wherein said tumor cells contain one to two million αGal epitopes.

2. The pharmaceutical composition of claim 1, wherein said αGal epitopes are synthesized on the surface of said tumor cells by transfecting said cells with an α(1,3) galactosyltransferase gene.

3. The pharmaceutical composition of claim 1, wherein said pre-existing tumor is selected from the group consisting of pancreas, prostate, lung and melanoma.

4. The pharmaceutical composition of claim 3 wherein said pre-existing tumor is a lung tumor.

5. The pharmaceutical composition of claim 4, wherein said tumor cell line is selected from the group consisting of lung tumor cell lines A549, NCI-H460, NCI-H520 and combinations thereof.

6. The pharmaceutical composition of claim 3, wherein said pre-existing tumor is a pancreatic tumor.

7. The pharmaceutical composition of claim 6, wherein said tumor cell line is selected from the group consisting of pancreatic tumor cell lines HPAF-II, PANC-1, ASPC-1, BxPC3 and combinations thereof.

8. The pharmaceutical composition of claim 3, wherein said pre-existing tumor is a melanoma tumor.

9. The pharmaceutical composition of claim 8, wherein said tumor cell line is selected from the group consisting of melanoma tumor cell lines A375, COL0829, G-361 and combinations thereof.

10. The pharmaceutical composition of claim 3, wherein said pre-existing tumor is a prostate tumor.

11. The pharmaceutical composition of claim 10, wherein said tumor cell line is selected from the group consisting of prostate cell lines PC-3, LNCaPFGC, MDAPca2b, DU145 and combinations thereof.

12. The pharmaceutical composition of claim 1, wherein said composition is derived from a master cell bank prepared by sorting a subpopulation of tumor cells having the highest expression of αGal epitopes.

* * * * *

SEQUENCE LISTING

<160> NUMBER OF SEQ ID NOS: 3

<210> SEQ ID NO 1
<211> LENGTH: 7703
<212> TYPE: DNA
<213> ORGANISM: Artificial Sequence
<220> FEATURE:
<223> OTHER INFORMATION: Retroviral vector pLNC-KG

<400> SEQUENCE: 1

```
tttgaaagac cccacccgta ggtggcaagc tagcttaagt aacgccactt tgcaaggcat      60
ggaaaaatac ataactgaga atagaaaagt tcagatcaag gtcaggaaca agaaacagc     120 tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca cccctcact cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tgcagcattc tccagtgggg    600
gctcgtccgg gatttggaga cccctgccca gggaccaccg acccaccacc gggaggtaag    660
ctggccagca acttatctgt gtctgtccga ttgtctagtg tctatgtttg atgttatgcg    720
cctgcgtctg tactagttag ctaactagct ctgtatctgg cggacccgtg gtggaactga    780
cgagttctga acaccggcc gcaacccctgg gagacgtccc agggactttg ggggccgttt    840
ttgtggcccg acctgaggaa gggagtcgat gtggaatccg accccgtcag gatatgtggt    900
tctggtagga gacgagaacc taaaacagtt cccgcctccg tctgaatttt tgctttcggt    960
ttggaaccga agccgcgcgt cttgtctgct gcagcgctgc agcatcgttc tgtgttgtct   1020
```

```
ctgtctgact gtgtttctgt atttgtctga aaattagggc cagactgtta ccactccctt    1080
aagtttgacc ttaggtcact ggaaagatgt cgagcggatc gctcacaacc agtcggtaga    1140
tgtcaagaag agacgttggg ttaccttctg ctctgcagaa tggccaacct ttaacgtcgg    1200
atggccgcga cacggcacct ttaaccgaga cctcatcacc caggttaaga tcaaggtctt    1260
ttcacctggc ccgcatggac acccagacca ggtcccctac atcgtgacct gggaagcctt    1320
ggcttttgac ccccctccct gggtcaagcc ctttgtacac cctaagcctc cgcctcctct    1380
tcctccatcc gccccgtctc tccccttga acctcctcgt tcgaccccgc ctcgatcctc    1440
cctttatcca gccctcactc cttctctagg cgccggaatt ccgatctgat caagagacag    1500
gatgaggatc gtttcgcatg attgaacaag atggattgca cgcaggttct ccggccgctt    1560
gggtggagag gctattcggc tatgactggg cacaacagac aatcggctgc tctgatgccg    1620
ccgtgttccg gctgtcagcg caggggcgcc cggttctttt tgtcaagacc gacctgtccg    1680
gtgccctgaa tgaactgcag gacgaggcag cgcggctatc gtggctggcc acgacgggcg    1740
ttccttgcgc agctgtgctc gacgttgtca ctgaagcggg aagggactgg ctgctattgg    1800
gcgaagtgcc ggggcaggat ctcctgtcat ctcaccttgc tcctgccgag aaagtatcca    1860
tcatggctga tgcaatgcgg cggctgcata cgcttgatcc ggctacctgc ccattcgacc    1920
accaagcgaa acatcgcatc gagcgagcac gtactcggat ggaagccggt cttgtcgatc    1980
aggatgatct ggacgaagag catcaggggc tcgcgccagc cgaactgttc gccaggctca    2040
aggcgcgcat gcccgacggc gaggatctcg tcgtgaccca tggcgatgcc tgcttgccga    2100
atatcatggt ggaaaatggc cgcttttctg gattcatcga ctgtggccgg ctgggtgtgg    2160
cggaccgcta tcaggacata gcgttggcta cccgtgatat tgctgaagag cttggcggcg    2220
aatgggctga ccgcttcctc gtgctttacg gtatcgccgc tcccgattcg cagcgcatcg    2280
ccttctatcg ccttcttgac gagttcttct gagcgggact ctggggttcg aaatgaccga    2340
ccaagcgacg cccaacctgc catcacgaga tttcgattcc accgccgcct tctatgaaag    2400
gttgggcttc ggaatcgttt tccgggacgc cggctggatg atcctccagc gcggggatct    2460
catgctggag ttcttcgccc accccgggct cgatccctc gcgagttggt tcagctgctg    2520
cctgaggctg gacgacctcg cggagttcta ccggcagtgc aaatccgtcg gcatccagga    2580
aaccagcagc ggctatccgc gcatccatgc ccccgaactg caggagtggg gaggcacgat    2640
ggccgctttg gtcgaggcgg atccggccat tagccatatt attcattggt tatatagcat    2700
aaatcaatat tggctattgg ccattgcata cgttgtatcc atatcataat atgtacattt    2760
atattggctc atgtccaaca ttaccgccat gttgacattg attattgact agttattaat    2820
agtaatcaat tacggggtca ttagttcata gcccatatat ggagttccgc gttacataac    2880
ttacggtaaa tggcccgcct ggctgaccgc ccaacgaccc ccgcccattg acgtcaataa    2940
tgacgtatgt tcccatagta acgccaatag ggactttcca ttgacgtcaa tgggtggagt    3000
atttacggta aactgcccac ttggcagtac atcaagtgta tcatatgcca agtacgcccc    3060
ctattgacgt caatgacggt aaatggcccg cctggcatta tgcccagtac atgaccttat    3120
gggactttcc tacttggcag tacatctacg tattagtcat cgctattacc atggtgatgc    3180
ggttttggca gtacatcaat gggcgtggat agcggtttga ctcacgggga tttccaagtc    3240
tccaccccat tgacgtcaat gggagtttgt tttggcacca aaatcaacgg gactttccaa    3300
aatgtcgtaa caactccgcc ccattgacgc aaatgggcgg taggcgtgta cggtgggagg    3360
tctatataag cagagctcgt ttagtgaacc gtcagatcgc ctggagacgc catccacgct    3420
```

```
gttttgacct ccatagaaga caccgggacc gatccagcct ccgcggcccc aagcttgaca    3480
tggatgtcaa gggaaaagta atcctgttga tgctgattgt ctcaaccgtg gttgtcgtgt    3540
tttgggaata tgtcaacaga attccagagg ttggtgagaa cagatggcag aaggactggt    3600
ggttcccaag ctggtttaaa aatgggaccc acagttatca agaagacaac gtagaaggac    3660
ggagagaaaa gggtagaaat ggagatcgca ttgaagagcc tcagctatgg gactggttca    3720
atccaaagaa ccgcccggat gttttgacag tgacccgtg aaggcgccg attgtgtggg    3780 aaggcactta tgacacagct ctgctggaaa agtactacgc cacacagaaa ctcactgtgg    3840
ggctgacagt gtttgctgtg gaaagtaca ttgagcatta cttagaagac tttctggagt    3900
ctgctgacat gtacttcatg gttggccatc gggtcatatt ttacgtcatg atagatgaca    3960
cctcccggat gcctgtcgtg cacctgaacc ctctacattc cttacaagtc tttgagatca    4020
ggtctgagaa gaggtggcag gatatcagca tgatgcgcat gaagaccatt ggggagcaca    4080
tcctggccca catccagcac gaggtcgact tcctcttctg catggacgtg gatcaagtct    4140
ttcaagacaa cttcggggtg gaaactctgg gccagctggt agcacagctc caggcctggt    4200
ggtacaaggc cagtcccgag aagttcacct atgagaggcg ggaactgtcg gccgcgtaca    4260
ttccattcgg agaggggat ttttactacc acgcggccat ttttggagga acgcctactc    4320
acattctcaa cctcaccagg gagtgcttta aggggatcct ccaggacaag aaacatgaca    4380
tagaagccca gtggcatgat gagagccacc tcaacaaata cttccttttc aacaaaccca    4440
ctaaaatcct atctccagag tattgctggg actatcagat aggcctgcct tcagatatta    4500
aaagtgtcaa ggtagcttgg cagacaaaag agtataattt ggttagaaat aatgtctgaa    4560
tcgataaaat aaaagatttt atttagtctc cagaaaaagg ggggaatgaa agaccccacc    4620
tgtaggtttg gcaagctagc ttaagtaacg ccattttgca aggcatggaa aaatacataa    4680
ctgagaatag agaagttcag atcaaggtca ggaacagatg gaacagctga atatgggcca    4740
aacaggatat ctgtggtaag cagttcctgc cccggctcag ggccaagaac agatggaaca    4800
gctgaatatg gccaaaacag gatatctgtg gtaagcagtt cctgccccgg ctcagggcca    4860
agaacagatg gtccccagat gcggtccagc cctcagcagt ttctagagaa ccatcagatg    4920
tttccagggt gccccaagga cctgaaatga ccctgtgcct tatttgaact aaccaatcag    4980
ttcgcttctc gcttctgttc gcgcgcttct gctccccgag ctcaataaaa gagcccacaa    5040
cccctcactc ggggcgccag tcctccgatt gactgagtcg cccgggtacc cgtgtatcca    5100
ataaaccctc ttgcagttgc atccgacttg tggtctcgct gttccttggg agggtctcct    5160
ctgagtgatt gactacccgt cagcgggggt cttcatttg gggctcgtc cgggatcggg    5220 agaccctgc ccagggacca ccgacccacc accgggaggt aagctggctg cctcgcgcgt    5280
ttcggtgatg acggtgaaaa cctctgacac atgcagctcc cggagacggt cacagcttgt    5340
ctgtaagcgg atgccgggag cagacaagcc cgtcagggcg cgtcagcggg tgttggcggg    5400
tgtcggggcg cagccatgac ccagtcacgt agcgatagcg gagtgtatac tggcttaact    5460
atgcggcatc agagcagatt gtactgagag tgcaccatat gcggtgtgaa ataccgcaca    5520
gatgcgtaag gagaaaatac cgcatcaggc gctcttccgc ttcctcgctc actgactcgc    5580
tgcgctcggt cgttcggctg cggcgagcgg tatcagctca ctcaaaggcg gtaatacggt    5640
tatccacaga atcaggggat aacgcaggaa agaacatgtg agcaaaaggc cagcaaaagg    5700
ccaggaaccg taaaaaggcc gcgttgctgg cgttttttcca taggctccgc cccctgacg    5760 agcatcacaa aaatcgacgc tcaagtcaga ggtggcgaaa cccgacagga ctataaagat    5820
```

```
accaggcgtt tccccctgga agctccctcg tgcgctctcc tgttccgacc ctgccgctta    5880
ccggatacct gtccgccttt ctcccttcgg gaagcgtggc gctttctcat agctcacgct    5940
gtaggtatct cagttcggtg taggtcgttc gctccaagct gggctgtgtg cacgaacccc    6000
ccgttcagcc cgaccgctgc gccttatccg gtaactatcg tcttgagtcc aacccggtaa    6060
gacacgactt atcgccactg gcagcagcca ctggtaacag gattagcaga gcgaggtatg    6120
taggcggtgc tacagagttc ttgaagtggt ggcctaacta cggctacact agaaggacag    6180

tatttggtat ctgcgctctg ctgaagccag ttaccttcgg aaaaagagtt ggtagctctt    6240
gatccggcaa acaaaccacc gctggtagcg gtggtttttt tgtttgcaag cagcagatta    6300
cgcgcagaaa aaaggatctc aagaagatcc tttgatcttt tctacggggt ctgacgctc    6360 agtggaacga aaactcacgt taagggattt tggtcatgag attatcaaaa aggatcttca    6420
cctagatcct tttaaattaa aatgaagttt taaatcaat ctaaagtata tatgagtaaa    6480
cttggtctga cagttaccaa tgcttaatca gtgaggcacc tatctcagcg atctgtctat    6540
ttcgttcatc catagttgcc tgactccccg tcgtgtagat aactacgata cgggagggct    6600

taccatctgg ccccagtgct gcaatgatac cgcgagaccc acgctcaccg gctccagatt    6660

tatcagcaat aaaccagcca gccggaaggg ccgagcgcag aagtggtcct gcaactttat    6720
ccgcctccat ccagtctatt aattgttgcc gggaagctag agtaagtagt tcgccagtta    6780
atagtttgcg caacgttgtt gccattgctg caggcatcgt ggtgtcacgc tcgtcgtttg    6840
gtatggcttc attcagctcc ggttcccaac gatcaaggcg agttacatga tcccccatgt    6900
tgtgcaaaaa agcggttagc tccttcggtc ctccgatcgt tgtcagaagt aagttggccg    6960
cagtgttatc actcatggtt atggcagcac tgcataattc tcttactgtc atgccatccg    7020
taagatgctt ttctgtgact ggtgagtact caaccaagtc attctgagaa tagtgtatgc    7080
ggcgaccgag ttgctcttgc ccggcgtcaa cacgggataa taccgcgcca catagcagaa    7140
ctttaaaagt gctcatcatt ggaaaacgtt cttcggggcg aaaactctca aggatcttac    7200
cgctgttgag atccagttcg atgtaaccca ctcgtgcacc caactgatct tcagcatctt    7260
ttactttcac cagcgtttct gggtgagcaa aaacaggaag gcaaaatgcc gcaaaaaagg    7320
gaataagggc gacacggaaa tgttgaatac tcatactctt ccттттттcaa tattattgaa    7380 gcatttatca gggttattgt tcatgagcg gatacatatt tgaatgtatt tagaaaaata    7440
aacaaatagg ggttccgcgc acatttcccc gaaaagtgcc acctgacgtc taagaaacca    7500

ttattatcat gacattaacc tataaaaata ggcgtatcac gaggcccttt cgtcttcaag    7560
aattcatacc agatcaccga aaactgtcct ccaaatgtgt ccccctcaca ctcccaaatt    7620
cgcgggcttc tgcctcttag accactctac cctattcccc acactcaccg gagccaaagc    7680
cgcggccctt ccgtttcttt gct                                            7703
```

<210> SEQ ID NO 2
<211> LENGTH: 36
<212> TYPE: DNA
<213> ORGANISM: Artificial Sequence
<220> FEATURE:
<223> OTHER INFORMATION: Forward primer

<400> SEQUENCE: 2
acaaaagctt gacatggatg tcaagggaaa agtaat                             36

<210> SEQ ID NO 3
<211> LENGTH: 28
<212> TYPE: DNA

```
<213> ORGANISM: Artificial Sequence
<220> FEATURE:
<223> OTHER INFORMATION: Reverse primer

<400> SEQUENCE: 3
aattatcgat tcagacatta tttctaac                                        28
```